US009815816B2

(12) United States Patent
Blixt et al.

(10) Patent No.: US 9,815,816 B2
(45) Date of Patent: Nov. 14, 2017

(54) CHEMICAL PROCESS FOR THE SYNTHESIS OF 4-(4-BROMO-2-FLUOROANILINO)-6-METHOXY-7-(1-METHYLPIPERIDIN-4-YLMETHOXY)QUINAZOLINE

(71) Applicant: AstraZeneca AB, Sodertalje (SE)

(72) Inventors: Jorgen Blixt, Sodertalje (SE); Michael David Golden, Macclesfield (GB); Philip John Hogan, Macclesfield (GB); David Michael Glanville Martin, Macclesfield (GB); Francis Joseph Montgomery, Macclesfield (GB); Zakariya Patel, Loughborough (GB); John David Pittam, Macclesfield (GB); George Joseph Sependa, Macclesfield (GB); Christopher John Squire, Macclesfield (GB); Nicholas Cartwright Alexander Wright, Macclesfield (GB)

(73) Assignee: Genzyme Corporation, Cambridge, MA (US)

(*) Notice: Subject to any disclaimer, the term of this patent is extended or adjusted under 35 U.S.C. 154(b) by 0 days.

(21) Appl. No.: 14/805,816

(22) Filed: Jul. 22, 2015

(65) Prior Publication Data
US 2016/0185754 A1 Jun. 30, 2016

Related U.S. Application Data

(60) Continuation of application No. 14/481,302, filed on Sep. 9, 2014, now abandoned, which is a division of application No. 13/314,034, filed on Dec. 7, 2011, now Pat. No. 8,865,899, which is a division of application No. 12/088,680, filed as application No. PCT/GB2006/003587 on Sep. 27, 2006, now Pat. No. 8,163,926.

(30) Foreign Application Priority Data

Sep. 30, 2005 (GB) .................... 0519879.1

(51) Int. Cl.
C07D 401/12 (2006.01)
C07D 211/16 (2006.01)
C07D 239/94 (2006.01)

(52) U.S. Cl.
CPC .......... C07D 401/12 (2013.01); C07D 211/16 (2013.01); C07D 239/94 (2013.01)

(58) Field of Classification Search
CPC ................................................ C07D 401/11
See application file for complete search history.

(56) References Cited

U.S. PATENT DOCUMENTS 5,763,458 A  6/1998  Clark et al.

FOREIGN PATENT DOCUMENTS

| CA | 2129374 A1 | 2/1995 |
|---|---|---|
| EP | 0317997 A2 | 5/1989 |
| EP | 0638567 A1 | 2/1995 |
| EP | 1481971 A1 | 12/2004 |
| WO | 92/06086 A1 | 4/1992 |
| WO | 92/17475 A1 | 10/1992 |
| WO | 92/20642 A1 | 11/1992 |
| WO | 94/19342 A1 | 9/1994 |
| WO | 94/27965 A1 | 12/1994 |
| WO | 95/15758 A1 | 6/1995 |
| WO | 95/19344 A1 | 7/1995 |
| WO | 97/22596 A1 | 6/1997 |
| WO | 97/32856 A1 | 9/1997 |
| WO | 98/10767 A2 | 3/1998 |
| WO | 98/13354 A1 | 4/1998 |
| WO | 01/32651 A1 | 5/2001 |
| WO | 03/039551 A1 | 5/2003 |
| WO | 03/053361 A2 | 7/2003 |
| WO | 03/064413 A1 | 8/2003 |
| WO | 2004/014383 A1 | 2/2004 |
| WO | 2005/013998 A1 | 2/2005 |

OTHER PUBLICATIONS

Hennequin et al., "Design and Structure Activity Relationship of a New Class of Potent VEGF Receptor Tyrosine Kinase Inhibitors," Journal of Medicinal Chemistry, American Chemical Society, 42: 5369-5389 (1999).

Hennequin et al., "Novel 4-anilinoquinazolines with C-7 basic side chains: Design and structure activity relationship of a series of potent, orally active, VEGF receptor tyrosine kinase inhibitors," Journal of Medicinal Chemistry, American Chemical Society, 45: 1300-1312 (2002).

Iyobe et al., "Studies on new platelet aggregation inhibitors 1. Synthesis of 7-Nitro-3,4-dihydroquinoline-2(1H)-one Derivatives," Chemical and Pharmaceutical Bulletin, 49: 822-829 (2001).

(Continued)

Primary Examiner — Paul V Ward
(74) Attorney, Agent, or Firm — Morgan, Lewis & Bockius LLP

(57) ABSTRACT

The present invention relates to chemical processes for the manufacture of certain quinazoline derivatives, or pharmaceutically acceptable salts thereof. The invention also relates to processes for the manufacture of certain intermediates useful in the manufacture of the quinazoline derivatives and to processes for the manufacture of the quinazoline derivatives utilizing said intermediates. In particular, the present invention relates to chemical processes and intermediates useful in the manufacture of the compound 4-(4-bromo-2-fluoroanilino)-6-methoxy-7-(1-methylpiperidin-4-yl-methoxy)quinazoline.

5 Claims, 1 Drawing Sheet

(56) References Cited

OTHER PUBLICATIONS

Lévesque et al., "Novel bicyclic lactam inhibitors of thrombin: Potency and selectivity optimization through P1 residues," Bioorganic & Medicinal Chemistry Letters, 11: 3161-3164 (2001).
Sardina et al., "Chirospecific synthesis of nitrogen and side chain modified analogues of (+)-anatoxin," Journal of Organic Chemistry, 54: 4654-4660 (1989).
Sutton et al., "Solid-phase synthesis and SAR of 4-carboxy-2-azetidinone mechanism-based tryptase inhibitors" Bioorganic & Medicinal Chemistry Letters, 14: 2233-2239 (2004).

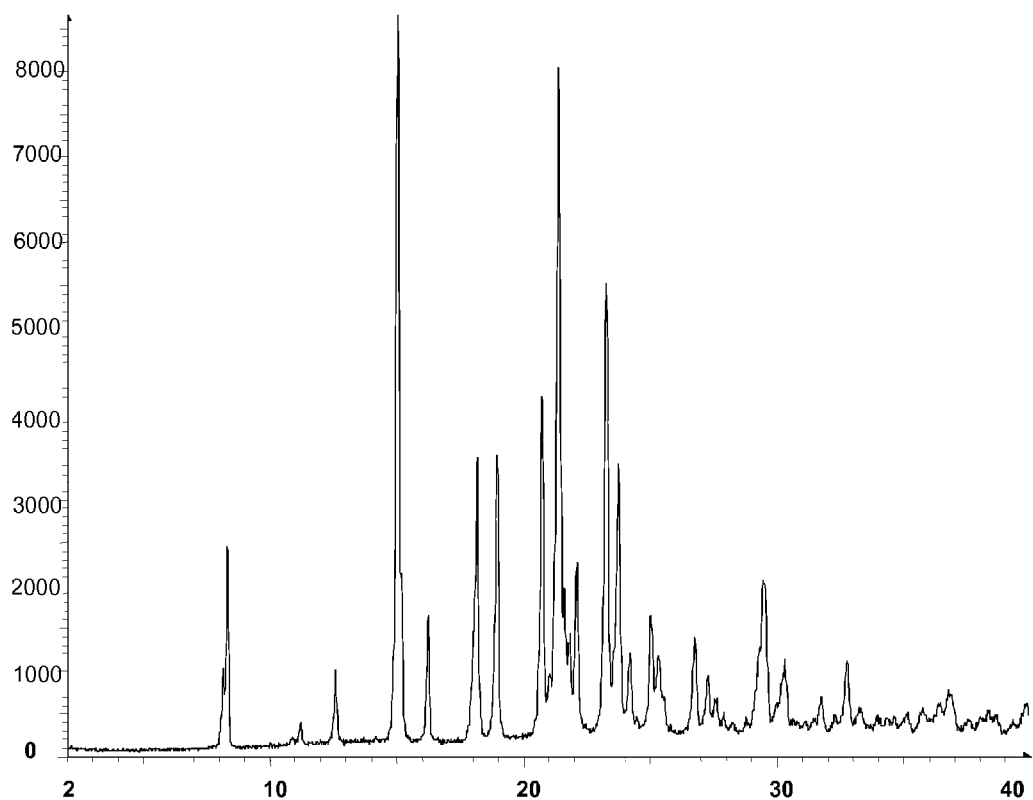

CHEMICAL PROCESS FOR THE SYNTHESIS OF 4-(4-BROMO-2-FLUOROANILINO)-6-METHOXY-7-(1-METHYLPIPERIDIN-4-YLMETHOXY)QUINAZOLINE

The present invention relates to chemical processes for the manufacture of certain quinazoline derivatives, or pharmaceutically acceptable salts thereof. The invention also relates to processes for the manufacture of certain intermediates useful in the manufacture of the quinazoline derivatives and to processes for the manufacture of the quinazoline derivatives utilising said intermediates.

In particular, the present invention relates to chemical processes and intermediates useful in the manufacture of the compound 4-(4-bromo-2-fluoroanilino)-6-methoxy-7-(1-methylpiperidin-4-ylmethoxy)quinazoline. This compound falls within the broad disclosure of WO 98/13354 and is exemplified in WO 01/32651, in Examples 2a, 2b and 2c.

The compound 4-(4-bromo-2-fluoroanilino)-6-methoxy-7-(1-methylpiperidin-4-ylmethoxy)quinazoline is described herein by way of the Formula I:

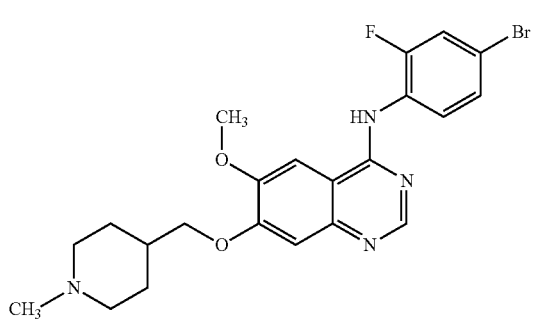

and as ZD6474, the code number by which the compound is known. The compound ZD6474 is also known as Vandetanib and as Zactima™.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57-66; Folkman, 1995, Nature Medicine 1: 27-31). Alteration of vascular permeability is thought to play a role in both normal and pathological physiological processes (Cullinan-Bove et al, 1993, Endocrinology 133: 829-837; Senger et al, 1993, Cancer and Metastasis Reviews, 12: 303-324). Several polypeptides with in vitro endothelial cell growth promoting activity have been identified including, acidic and basic fibroblast growth factors (aFGF & bFGF) and vascular endothelial growth factor (VEGF). By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848-859; Kolch et al, 1995, Breast Cancer Research and Treatment, 36:139-155) and vascular permeability (Connolly et al, 1989, J. Biol. Chem. 264: 20017-20024). Antagonism of VEGF action by sequestration of VEGF with antibody can result in inhibition of tumour growth (Kim et al, 1993, Nature 362: 841-844).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity which leads to phosphorylation of tyrosine residues on both the receptor and other intracellular molecules. These changes in tyrosine phosphorylation initiate a signalling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt-1 (also referred to as VEGFR-1), the kinase insert domain-containing receptor, KDR (also referred to as VEGFR-2 or Flk-1), and another fms-like tyrosine kinase receptor, Flt-4. Two of these related RTKs, Flt-1 and KDR, have been shown to bind VEGF with high affinity (De Vries et al, 1992, Science 255: 989-991; Terman et al, 1992, Biochem. Biophys. Res. Comm. 1992, 187: 1579-1586). Binding of VEGF to these receptors expressed in heterologous cells has been associated with changes in the tyrosine phosphorylation status of cellular proteins and calcium fluxes.

VEGF is a key stimulus for vasculogenesis and angiogenesis. This cytokine induces a vascular sprouting phenotype by inducing endothelial cell proliferation, protease expression and migration, and subsequent organisation of cells to form a capillary tube (Keck, P. J., Hauser, S. D., Krivi, G., Sanzo, K., Warren, T., Feder, J., and Connolly, D. T., Science (Washington D.C.), 246: 1309-1312, 1989; Lamoreaux, W. J., Fitzgerald, M. E., Reiner, A., Hasty, K. A., and Charles, S. T., Microvasc. Res., 55: 29-42, 1998; Pepper, M. S., Montesano, R., Mandroita, S. J., Orci, L. and Vassalli, J. D., Enzyme Protein, 49: 138-162, 1996). In addition, VEGF induces significant vascular permeability (Dvorak, H. F., Detmar, M., Claffey, K. P., Nagy, J. A., van de Water, L., and Senger, D. R., (Int. Arch. Allergy Immunol., 107: 233-235, 1995; Bates, D. O., Heald, R. I., Curry, F. E. and Williams, B. J. Physiol. (Lond.), 533: 263-272, 2001), promoting formation of a hyper-permeable, immature vascular network which is characteristic of pathological angiogenesis.

It has been shown that activation of KDR alone is sufficient to promote all of the major phenotypic responses to VEGF, including endothelial cell proliferation, migration, and survival, and the induction of vascular permeability (Meyer, M., Clauss, M., Lepple-Wienhues, A., Waltenberger, J., Augustin, H. G., Ziche, M., Lanz, C., Büttner, M., Rziha, H-J., and Dehio, C., EMBO J., 18: 363-374, 1999; Zeng, H., Sanyal, S. and Mukhopadhyay, D., J. Biol. Chem., 276: 32714-32719, 2001; Gine, H., Kowalski, J., Li, B., LeCouter, J., Moffat, B, Zioncheck, T. F., Pelletier, N. and Ferrara, N., J. Biol. Chem., 276: 3222-3230, 2001).

ZD6474 is a potent inhibitor of VEGF RTK and also has some activity against epidermal growth factor (EGF) RTK. ZD6474 inhibits the effects of VEGF and is of interest for its antiangiogenic and/or vascular permeability effects. Angiogenesis and/or an increase in vascular permeability is present in a wide range of disease states including cancer (including leukaemia, multiple myeloma and lymphoma), diabetes, psoriasis, rheumatoid arthritis, Kaposi's sarcoma, haemangioma, acute and chronic nephropathies, atheroma, arterial restenosis, autoimmune diseases, acute inflammation, excessive scar formation and adhesions, lymphoedema, endometriosis, dysfunctional uterine bleeding and ocular diseases with retinal vessel proliferation including agerelated macular degeneration. ZD6474 has been shown to elicit broad-spectrum anti-tumour activity in a range of models following once-daily oral administration (Wedge S. R., Ogilvie D. J., Dukes M. et al, Proc. Am. Assoc. Canc. Res. 2001; 42: abstract 3126).

WO 98/13354 discloses several possible routes for preparing 4-anilino quinazoline compounds. However, there is no specific disclosure in WO 98/13354 of a process for preparing a compound of the Formula I.

WO 98/10767 also discloses several possible routes for preparing 4-anilino quinazoline compounds. However, there is no specific disclosure in WO 98/10767 of a process for preparing a compound of the Formula I.

WO 01/32651 discloses several alternative routes for preparing a compound of the Formula I.

The route that is disclosed in Example 2a of WO 01/32651 involves the reaction of the compound 4-(4-bromo-2-fluoroanilino)-6-methoxy-7-(piperidin-4-ylmethoxy)quinazoline with aqueous formaldehyde, followed by sodium cyanoborohydride in a solvent mixture of tetrahydrofuran and methanol. The product is purified by chromatography and isolated as the free base. The free base is then converted to the hydrochloride salt by reaction with hydrogen chloride in a solvent mixture of methylene chloride and methanol.

The route that is disclosed in Example 2b of WO 01/32651 involves the reaction of the compound 4-(4-bromo-2-fluoroanilino)-6-methoxy-7-(1-(tert-butoxycarbonyl)piperidin-4-ylmethoxy)quinazoline with aqueous formaldehyde in formic acid, followed by reaction with sodium hydroxide in water and extraction of the product with ethyl acetate. The product is in the form of the free base.

The route that is disclosed in Example 2c of WO 01/32651 involves the reaction of the compound 4-chloro-6-methoxy-7-(1-methylpiperidin-4-ylmethoxy)quinazoline with 4-bromo-2-fluoroaniline and hydrogen chloride in isopropanol. The product that is isolated is in the form of the hydrochloride salt. In an NMR experiment, the hydrochloride salt is dissolved in dimethylsulfoxide and converted to the free base by adding solid potassium carbonate. The free base is then converted to the trifluoroacetate salt by adding trifluoroacetic acid. In another experiment, the hydrochloride salt is suspended in methylene chloride and washed with saturated sodium hydrogen carbonate to provide the free base.

WO 01/32651 also discloses routes for preparing the starting materials that are used in Examples 2a, 2b and 2c, such as the compounds 4-(4-bromo-2-fluoroanilino)-6-methoxy-7-(piperidin-4-ylmethoxy)quinazoline, 4-(4-bromo-2-fluoroanilino)-6-methoxy-7-(1-(tert-butoxycarbonyl)piperidin-4-ylmethoxy)quinazoline and 4-chloro-6-methoxy-7-(1-methylpiperidin-4-ylmethoxy)quinazoline. Several of these routes are discussed in more detail below.

The routes described in WO 01/32651 for preparing ZD6474 (as the hydrochloride salt or the free base) are also described and/or referenced in publications relating to combination therapies including ZD6474, such as WO 03/039551, WO 2004/014383, WO 2004/014426, WO 2004/032937, WO 2004/071397 and WO 2005/004870.

The existing routes for preparing the compound of the Formula I are satisfactory for the synthesis of relatively small amounts of the compound. However, the routes involve linear rather than convergent synthesis, requiring the use of multiple purification steps and the isolation of a substantial number of intermediates. As such, the overall yield of the synthesis is not high. There is, therefore, a need for a more efficient synthesis of the compound of the Formula I suitable for use to make larger quantities of that compound. There is also a need for more efficient syntheses of the intermediate compounds useful in the synthesis of the compound of the Formula I for use to make larger quantities of those intermediate compounds.

Preferably, the new syntheses should minimise the number of intermediate compounds that need to be isolated and should not involve costly and time-consuming purification procedures. Additionally, the new syntheses should form consistently high quality compounds, in particular so as to form a high quality compound of the Formula I to satisfy the high purity requirements of a pharmaceutical product. The new syntheses should also use procedures and reagents that can safely be used in a manufacturing plant and that meet environmental guidelines.

According to the present invention, we now provide improved processes for the manufacture of ZD6474, the compound of the Formula I.

According to the present invention, processes are also provided for the manufacture of key intermediate compounds that may be used in the manufacture of ZD6474.

The new processes are advantageous in that they allow the compounds to be made in high quality and high yield on a larger scale. The processes allow a substantial reduction in the number of intermediate compounds that must be isolated and, in general, are more convergent than the previous routes. Such changes provide significant advantages of time and cost.

For the avoidance of doubt, the term "ZD6474" as used hereinafter refers to the ZD6474 free base, unless otherwise stated.

A key intermediate that may be used in the preparation of ZD6474 is a compound of Formula IIa

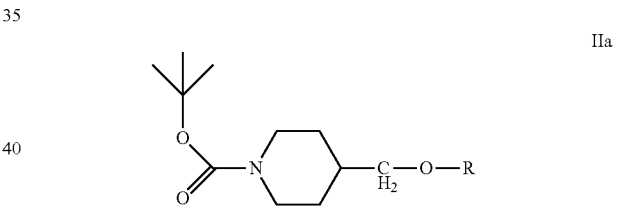

IIa

Wherein R is a suitable sulphonate ester such as mesylate, esylate, besylate or tosylate.

In a further embodiment the compound of Formula IIa is 1-(tert-butoxycarbonyl)-4-(4-methylphenylsulfonyloxymethyl)piperidine, the compound of the Formula II:

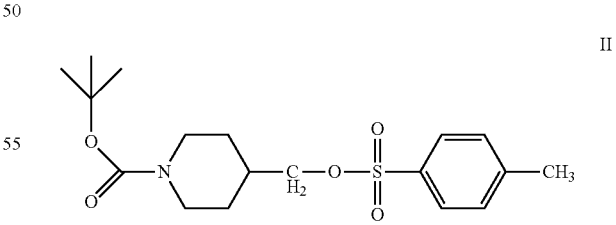

II

Example 2 of WO 01/32651 discloses a route for the preparation of a compound of the Formula II. The route involves the reaction of ethyl 4-piperidinecarboxylate with di-tert-butyl dicarbonate in an ethyl acetate solvent to provide ethyl 4-(1-(tert-butoxycarbonyl)piperidine)carboxylate, which is isolated. The ethyl 4-(1-(tert-butoxycarbonyl)piperidine)carboxylate is then reacted with lithium aluminium hydride in tetrahydrofuran to provide 1-(testbutoxycarbonyl)-4-hydroxymethylpiperidine, which is isolated. The 1-(tert-butoxycarbonyl)-4-hydroxymethylpiperidine is then reacted with 1,4-diazabicyclo[2.2.2]octane and toluene sulfonyl chloride in a tert-butyl methyl ether solvent to provide the compound of the Formula II.

EP-A-0317997 discloses a route for the preparation of a compound of the Formula II. The route involves the reaction of 4-carboxypiperidine (also known as isonipecotic acid) with sodium carbonate and di-tert-butyl dicarbonate in a water solvent to provide 4-carboxy-piperidine-1-carboxylic acid tert-butyl ester, which is isolated. The 4-carboxy-piperidine-1-carboxylic acid tert-butyl ester is then reacted with borane in a tetrahydrofuran solvent to provide the compound of the Formula II.

WO 94/27965 discloses a route for the preparation of a compound of the Formula II. The route involves the reaction of 4-hydroxymethylpiperidine with di-tert-butyl dicarbonate in a tetrahydrofuran solvent to provide tert-butyl 4-(hydroxymethyl)piperidine-1-carboxylate, which is isolated as an oil. The 1-(tert-butoxycarbonyl)-4-hydroxymethylpiperidine is then reacted with toluene sulfonyl chloride and pyridine to provide the compound of the Formula II.

The routes disclosed in the prior art documents for the preparation of a compound of the Formula II are satisfactory for the synthesis of relatively small amounts of the compound. However, they all require each of the intermediates to be isolated and, therefore, include multiple isolation and/or purification steps. This results in a satisfactory overall yield of the compound of the Formula II on the small scale used. However, the routes disclosed in the prior art documents are unsuitable for use on a manufacturing scale because they include multiple isolation and/or purification steps, which cannot be conducted efficiently on a manufacturing scale. In particular, the routes disclosed in the prior art documents are unsuitable for use in the manufacture of a high purity pharmaceutical product.

There is, therefore, a need for a more efficient synthesis of a compound of the Formula II suitable for use to make larger quantities of that compound. Preferably, the new synthesis should not involve costly and time-consuming isolation and/or purification procedures. Thus, the new synthesis should reduce the number of isolation and/or purification procedures required, thereby reducing costs and time of manufacture. Preferably, the new synthesis should minimise the number of solvents used throughout the process, which improves environmental performance and provides the opportunity for solvent recovery. Preferably, the new synthesis should also provide a robust and reliable method of isolating the compound of the Formula II and consistently should provide high quality compound of the Formula II, for example so as to satisfy the regulatory requirements for the introduction of starting materials into the production of pharmaceutical products.

According to a first aspect of the present invention, there is provided a process for the manufacture of a compound of the Formula IIa from a (C1-C6)alkyl-4-piperidinecarboxylate compound of the Formula III:

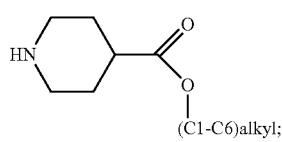

which process comprises the steps of:
(a) reacting the (C1-C6)alkyl-4-piperidinecarboxylate compound of the Formula III with di-tert-butyl dicarbonate in the presence of toluene or xylene to form a first mixture comprising toluene or xylene, tert-butanol and a compound of the Formula IV:

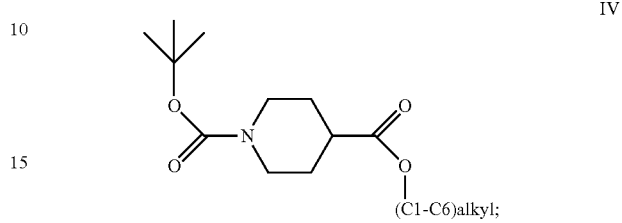

(b) substantially removing the text-butanol from the first mixture;
(c) reacting the compound of the Formula IV with a suitable reducing agent in situ in the presence of toluene or xylene to form a second mixture comprising toluene, reduction by-products including alcohol by-products and a compound of the Formula V:

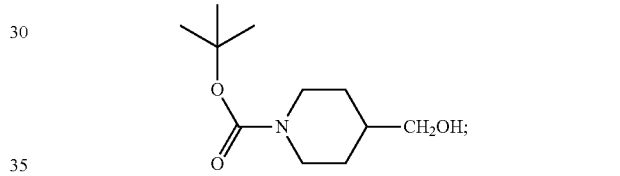

(d) substantially removing the alcohol by-products from the second mixture; and
(e) reacting the compound of the Formula V with a suitable sulphonating agent in situ to form a sulphonate ester in the presence of a suitable base and toluene to form the compound of the Formula IIa.

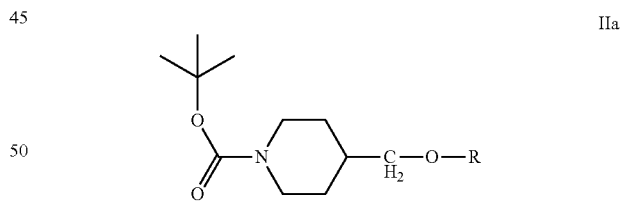

wherein R is a suitable sulphonate ester such as mesylate, esylate, besylate or tosylate. In one embodiment the sulphonating agent is tosyl chloride.

For avoidance of doubt the term 'in situ' means that the reaction was performed without isolation of the reactants from the previous process step.

The process of the first aspect of the present invention is advantageous in that it allows a compound of the Formula IIa to be made in high quality and high yield on a larger scale. Typically, each of the steps of the process of the first aspect of the present invention proceeds in greater than 95% yield.

All steps of the process of the first aspect of the present invention are conducted in toluene or xylene as the solvent.

In another embodiment all the steps of the first aspect of the present invention are conducted in toluene. This allows the process to be conducted as a continuous process without isolation and/or purification of the intermediate compounds of the Formulae IV and V. This significantly reduces the time and cost of manufacturing the compound of the Formula IIa on a larger scale. The use of a single solvent such as toluene or xylene may also allow for solvent recycling, which increases the efficiency of the process and provides environmental benefits. The use of toluene or xylene as the solvent also allows for the efficient and convenient removal of reactive by-products (such as alcohols), for example by distillation. The presence of such reactive by-products could lead to impurities in the compound of the Formula IIa if not removed at the appropriate time.

Additionally, the use of toluene or xylene as the solvent in the process of the first aspect of the present invention allows for the convenient isolation of the compound of the Formula IIa by crystallisation. The compound of the Formula IIa may, for example, be isolated in greater than 99.5% purity by crystallisation directly from the reaction mixture without the need for further purification. This is advantageous, for example when the compound of the Formula IIa is to be introduced at a late stage into the production of a pharmaceutical product, for example a compound of the Formula I, because it minimises the risk of impurities being introduced into the pharmaceutical product.

Step (a) of the process uses a (C1-C6)alkyl-4-piperidinecarboxylate compound of the Formula III, particularly a (C1-C4)alkyl-4-piperidinecarboxylate compound of the Formula III. In particular, a suitable (C1-C6)alkyl-4-piperidinecarboxylate compound of the Formula III that may be used in step (a) may, for example, be ethyl 4-piperidinecarboxylate. Another name for ethyl 4-piperidine carboxylate is ethyl isonipecotate.

The reaction of step (a) is carried out at a temperature in the range, for example, of from 0 to 45° C., conveniently in the range of from 15 to 35° C., more conveniently in the range of from 25 to 30° C.

The (C1-C6)alkyl-4-piperidinecarboxylate compounds of the Formula III and the di-test-butyl dicarbonate starting material used in step (a) of the process are commercially available or can be prepared using conventional methods. For example, the (C1-C6)alkyl-4-piperidinecarboxylate compounds of the Formula III may be prepared as described in Japanese patent application number JP 03002162 A2.

The tert-butanol that is formed in step (a) is a by-product of the reaction between the (C1-C6)alkyl-4-piperidinecarboxylate compound of the Formula III and the di-tert-butyl dicarbonate. In the process of the present invention, this by-product is easily and conveniently substantially removed from the reaction mixture, for example by distillation in step (b).

It is advantageous to substantially remove the tert-butanol by-product from the reaction mixture, for example by distillation in step (b) because any tert-butanol by-product that is not removed is likely to react with the reducing agent in step (c), thereby reducing the amount of the reducing agent available for the desired reaction with the compound of the Formula IV. Thus, removal of the tert-butanol by-product in step (b) allows for the correct stoichiometry of the reagents in step (c) of the process and, therefore, a more efficient reaction in that step. This is turn provides a high yield and purity of the compound of the Formula V in step (c).

By the term "substantially removed" we mean that at least 85% of the tert-butanol by-product that is formed in step (a) is removed, for example by distillation. Typically, the distillation is conducted until an internal temperature in the range of between 102 to 112° C. is achieved. The distillation in step (b) is conveniently conducted at either atmospheric or partially reduced pressure.

Suitable reducing agents for use in step (c) include sodium bis(2-methoxyethoxy)aluminium hydride, lithium aluminium hydride and diisobutylaluminium hydride. More particularly, the reducing agent used in step (c) is sodium bis(2-methoxyethoxy)aluminium hydride.

The reaction of step (c) is carried out at a temperature in the range, for example, of from 20 to 55° C., conveniently in the range of from 30 to 50° C., more conveniently in the range of from 35 to 45° C.

As the skilled person would appreciate, the reaction of step (c) typically provides reduction by-products in addition to the desired compound of the Formula V. The reduction by-products include alcohol by-products. The alcohol by-products originate from the —O—(C1-C6)alkyl portion of the ester group in the compound of the Formula IV and may also originate from the reducing agent. For example, when the compound of the Formula IV is ethyl 4-(1-tert-butoxycarbonyl)piperidine)carboxylate and the reducing agent used in step (c) is sodium bis(2-methoxyethoxy)aluminium hydride, typical reduction by-products include aluminium salts and alcohol by-products such as ethanol and 2-methoxyethanol. The alcohol by-products are easily and conveniently substantially removed from the reaction mixture for example by distillation in step (d).

It is advantageous to substantially remove the alcohol by-products in step (d) because any such by-products that are not removed are likely to react with the sulphonating agent in step (e), thereby creating impurities that could contaminate the desired product and reducing the amount of sulphonating agent available for the desired reaction with the compound of the Formula V. Thus, removal of the alcohol by-products allows for the correct stoichiometry of the reagents in step (e) of the process and, therefore, a more efficient reaction in that step. This is turn provides a high yield and purity of the compound of the Formula II in step (e).

By the term "substantially removed" we mean that at least 98% of the alcohol by-products that are formed in step (c) are removed for example by distillation. Typically, the distillation is conducted until an internal temperature in the range of from between 102° C. to 112° C. is achieved. The distillation in step (d) is conveniently conducted at either atmospheric or partially reduced pressure.

The distillation in step (d) also typically substantially removes any water that is present. This again allows for the correct stoichiometry of the reagents in step (e) of the process because any water that is not removed is likely to react with the sulphonating agent in step (e), thereby reducing the amount of the sulphonating agent available for the desired reaction with the compound of the Formula V. By the term "substantially removed" we mean that less than 20 mol % of water remains after the distillation.

As the skilled person would appreciate, it is typically necessary to quench the reaction mixture in step (c) to remove any unreacted reducing agent that is present before the reaction in step (e) is conducted. Typically, the quench step also removes some of the reduction by-products listed above, for example the aluminium salts and some, but not all, of the alcohol by-products. Suitable quenching agents may in general be chosen from any agent that is described in the literature and/or that is known to the skilled person. For example, when the reducing agent used in step (c) is sodium bis(2-methoxyethoxy)aluminium hydride, the quenching agent typically may be an aqueous solution of potassium sodium tartrate (also known as Rochelle salt). Typically, the resulting aqueous phase (containing the quenched reducing agent) is then removed by separation. The quench step is conducted before the distillation in step (d).

A suitable base for use in step (e) is a tertiary amine base, for example triethylenediamine.

The reaction of step (e) is carried out at a temperature in the range, for example, of from 15 to 45° C., more conveniently in the range of from 25 to 35° C.

As the skilled person would appreciate, it is typically necessary to quench the reaction mixture in step (e) to remove any unreacted sulphonating agent that is present. Suitable quenching agents may in general be chosen from any agent that is described in the literature and/or that is known to the skilled person. For example, a suitable quenching agent may be a base such as sodium hydroxide or potassium carbonate.

In one aspect, the process for the manufacture of a compound of the Formula II may further include the step (f) of isolating and/or purifying the compound of the Formula II. The step (f) may comprise any suitable steps or procedures for isolating the desired product that are described in the literature and/or that are known to the skilled person. Particular steps that would be of use would provide high quality and high purity product. For example, the step (f) may comprise the steps of washing the compound of the Formula II with water and/or aqueous citric acid. The step (f) may, for example, also comprise crystallisation using a suitable solvent system. An example of a suitable solvent system is a solvent system comprising toluene and isohexane, which provides a compound of the Formula II in a high purity, typically in a purity of greater than 98%, conveniently greater than 99.5%, and in a high yield, typically in a yield of greater than 80%, conveniently greater than 85%. As a skilled person would appreciate, the step (f) may also comprise the step of temperature cycling (also referred to as "Ostwald ripening") the compound of the Formula II, so as to improve the physical form of the product, if necessary.

Another key intermediate that may be used in the preparation of ZD6474 is a protected derivative of 7-hydroxy-4-(4-bromo-2-fluoroanilino)-6-methoxyquinazoline, the compound of the Formula VI:

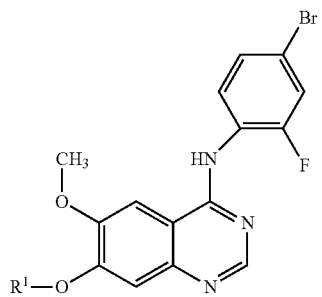

wherein R¹ is an acid labile protecting group, such as benzyl, substituted benzyl, tert-butyl, allyl or methoxyethoxymethyl.

Example 2 of WO 01/32651 and Example 24 of WO 97/32856 each disclose a route for the preparation of a hydrochloride salt of a compound of the Formula VI wherein R¹ is benzyl. The route involves the reaction of a hydrochloride salt of 7-benzyloxy-4-chloro-6-methoxyquinazoline with 4-bromo-2-fluoroaniline in a 2-propanol solvent to provide the hydrochloride salt of the compound of the Formula VI, which is isolated. It is stated in Example 2 of WO 01/32651 that the hydrochloride salt of 7-benzyloxy-4-chloro-6-methoxyquinazoline is prepared according to Example 1 of WO 97/22596. In Example 1 of WO 97/22596, the hydrochloride salt of 7-benzyloxy-4-chloro-6-methoxyquinazoline is prepared by the reaction of 7-benzyloxy-6-methoxy-3,4-dihydroquinazolin-4-one with thionyl chloride in a N,N-dimethylformamide solvent. The same process for the preparation of the hydrochloride salt of 7-benzyloxy-4-chloro-6-methoxyquinazoline is disclosed in Example 4 of WO 97/32856.

WO 98/10767 discloses a route for the preparation of 6,7-disubstituted 4-anilinoquinazoline compounds. The route involves the reaction of a 6,7-disubstituted quinazolinone compound with a chlorinating agent and a catalyst in the absence of a solvent or with a chlorinating agent in the presence of a trapping agent to provide a 6,7-disubstituted 4-chloroquinazoline compound. The 6,7-disubstituted 4-chloroquinazoline compound is then reacted with a substituted aniline compound, optionally in the presence of a suitable base, to provide a hydrochloride salt of the 6,7-disubstituted 4-anilinoquinazoline compound, which may then be converted to the free base. There is no disclosure in WO 98/10767 of 7-benzyloxy-4-(4-bromo-2-fluoroanilino)-6-methoxyquinazoline or of a process for its preparation.

The routes disclosed in the prior art documents for the preparation of a compound of the Formula VI are satisfactory for the synthesis of relatively small amounts of the compound. However, they all require the isolation and/or purification of intermediate compounds. This results in a satisfactory, but not high, overall yield of the compound of the Formula VI.

There is, therefore, a need for a more efficient synthesis of a compound of the Formula VI suitable for use to make larger quantities of that compound. Preferably, the new synthesis should not involve costly and time-consuming isolation and/or purification procedures. Thus, the new synthesis should reduce the number of isolation and/or purification procedures required, thereby reducing costs and time of manufacture. The new synthesis should also allow for effective isolation of the compound of the Formula VI in a crystalline form in high purity and yield, which crystalline form should have good filtration characteristics.

According to a second aspect of the present invention, there is provided a process for the manufacture of a compound of the Formula VI:

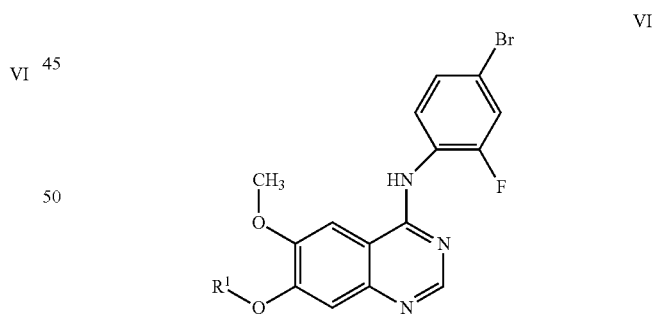

wherein R¹ is an acid labile protecting group; from a compound of the Formula VII:

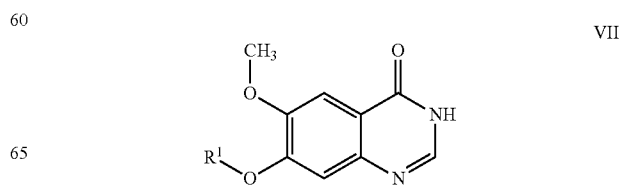

which process comprises the steps of
(g) reacting the compound of the Formula VII with a suitable chlorinating agent in the presence of a suitable base and a suitable solvent, wherein the reaction is carried out by:
- (g-1) adding a mixture of the compound of the Formula VII and the base in the solvent to a mixture of the chlorinating agent in the solvent at a temperature in the range of from 60 to 110° C., conveniently 60 to 80° C. over a period of about 60 minutes; or
- (g-2) adding the chlorinating agent to a mixture of the compound of the Formula VII and the base in the solvent at ambient temperature over a period of about 15 minutes and then heating the reaction mixture over a period of about 90 minutes to a temperature in the range of from 70 to 90° C. and stirring the reaction mixture at that temperature for about 1 hour; or
- (g-3) adding the chlorinating agent to a mixture of the compound of the Formula VII and the base in the solvent at a temperature in the range of from 60 to 110° C., conveniently 70 to 90° C. over a period of about 15 minutes, to form a compound of the Formula VIII:

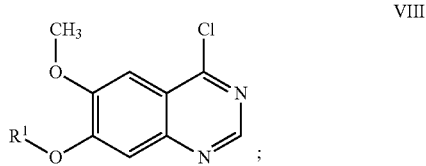

and
(h) reacting the compound of the Formula VIII with 4-bromo-2-fluoroaniline in situ in the presence of the solvent used in step (g) to form a hydrochloride salt of the compound of the Formula VI;
and whereafter the compound of the Formula VI obtained in the form of the hydrochloride salt may be converted into the free base or into the form of an alternative salt, if necessary.

The term 'acid labile protecting group' refers to groups which are readily removed under acidic conditions. Suitable methods for protection are those known to those skilled in the art. Conventional protecting groups may be used in accordance with standard practice (for illustration see T. W. Green, Protective Groups in Organic Synthesis, John Wiley and Sons, 1991). Suitable protecting groups at $R^1$ include benzyl, substituted benzyl (for example $C_{1-4}$alkoxybenzyl and $C_{1-4}$alkybenzyl), tert-butyl, 1, 1-dimethyl-1-ethylmethyl, allyl, substituted allyl (such as $C_{1-4}$alkylallyl) or methoxyethoxymethyl. In another embodiment $R^1$ is benzyl.

The process of the second aspect of the invention is advantageous in that it allows a compound of the Formula VI to be made in high purity and high yield on a larger scale. Typically, each of the steps of the process of the second aspect of the present invention proceeds in greater than 90% yield.

A suitable solvent for step (g) is selected from an aryl alkyl ether, such as anisole, a dialkyl ether such as 1,2-dimethyl ether, a halo substituted benzene such as chlorobenezene or trifluorotoluene or an alkyl substituted benzene such as xylene, ethyl benzene or toluene. In one embodiment of the invention the solvent for step (g) is anisole or toluene. In another embodiment of the invention the solvent for step (g) is toluene.

Steps (g) and (h) are both conducted in the same solvent, which solvent is selected from a suitable solvent as described above. This allows the process to be conducted as a continuous process without isolation and/or purification of the intermediate compound of the Formula VIII. This significantly reduces the time and cost of manufacturing the compound of the Formula VI on a larger scale. Additionally, the use of a single solvent may allow for solvent recycling, which increases the efficiency of the process and provides environmental benefits. The use of toluene or anisole as the reaction solvent is advantageous because these solvents minimise the formation of by-products that may be derived by dimerisation of the compound of the Formula VII, as discussed above. The choice of solvent also allows for the easy and convenient isolation of the compound of the Formula VI. For example, when the reaction mixture is cooled to ambient temperature, the compound of the Formula VI typically forms a solid, which solid may then be collected by any conventional method.

The mode of addition of the reagents in step (g) (i.e. as described in steps (g-1), (g-2) and (g-3)) is advantageous because it minimises the formation of by-products/impurities in that step. Typically, any such by-products/impurities are predominantly formed by dimerisation of the compound of the Formula VII. Reducing the formation of by-products/impurities enables the intermediate compound of the Formula VIII produced in step (g) to be used in step (h) without isolation and/or purification. Reducing the formation of by-products/impurities in step (g) also allows for the correct stoichiometry of the reagents in step (h) of the process and, therefore, a more efficient reaction in that step. This is turn provides a high yield and high purity of the compound of the Formula VI in step (h).

In one aspect of the invention, steps (g) and (h) are both conducted in toluene as the solvent. In another aspect of the invention, steps (g) and (h) are both conducted in anisole as the solvent. In yet another aspect of the invention, steps (g) and (h) are conducted in a solvent mixture of toluene and anisole.

A suitable chlorinating agent for use in step (g) is phosphorus oxychloride. Typically, in step (g), a molar excess of chlorinating agent is used relative to the compound of the Formula VII. For example, a molar excess in the range of from 1.3 to 2.0, conveniently in the range of from 1.7 to 1.8, may be used.

A suitable base for use in step (g) is a base selected from triethylamine and N,N-diisopropylethylamine. In particular, the base is N,N-diisopropylethylamine. The use of N,N-diisopropylethylamine as the base in step (g) is advantageous because it minimises the formation of by-products that may be derived by dimerisation of the compound of the Formula VII, as discussed above (for example as compared to the use of triethylamine as the base in step (g)). Adding a source of chloride to the reaction mixture (such as, for example, triethylamine hydrochloride) may also reduce the formation of such by-products.

In step (g-1), the reaction is carried out at a temperature in the range of from 60 to 110° C., conveniently 60 to 80° C., conveniently in the range of from 65 to 80° C., more conveniently in the range of from 70 to 75° C.

In step (g-2), the addition of reagents is carried out at ambient temperature. By the term "ambient temperature" we mean a temperature in the range of from 10 to 30° C., especially a temperature in the range of from 15 to 25° C., more especially a temperature of about 20° C. The reaction mixture is then heated to a temperature in the range of from 70 to 90° C., conveniently in the range of from 75 to 85° C., more conveniently in the range of from 80 to 85° C.

In step (g-3), the reaction is carried out at a temperature in the range of from 60 to 110° C., conveniently 70 to 90° C., conveniently in the range of from 75 to 85° C., more conveniently in the range of from 80 to 85° C.

In step (g), the term "of about" is used in the expressions "of about 60 minutes", "of about 15 minutes", "of about 90 minutes and "of about 1 hour" to indicate that the time periods quoted should not be construed as being absolute values because, as will be appreciated by those skilled in the art, the time periods may vary slightly. For example, the time periods quoted may vary by ±50%, particularly by ±15%, particularly by ±10% from the values quoted in step (g).

As the skilled person would appreciate, in step (g), the mixture of the compound of the Formula VII and the base in a suitable solvent will typically take the form of a suspension. The mixture of the chlorinating agent in a solvent selected from toluene and anisole will typically take the form of a solution. However, a number of factors may cause these forms to vary. Such factors may, for example, include the amount of each of the reagents added to the solvent, the particular base or chlorinating agent selected for use in step (g) and/or the temperature selected for use in step (g).

The reaction of step (h) is carried out at a temperature in the range of from 60 to 85° C., conveniently in the range of from 65 to 80° C., more conveniently in the range of from 70 to 75° C.

In one aspect of the invention, following step (h) of the process, the compound of the Formula VI is used directly in another process (for example, in a process for manufacturing 7-hydroxy-4-(4-bromo-2-fluoroanilino)-6-methoxyquinazoline as discussed below). In another aspect of the invention, following step (h) of the process, the compound of the Formula VI is isolated and/or purified, for example before storage, handling and/or further reaction. Therefore, in one aspect of the invention, the process for manufacturing a compound of the Formula VI further includes the step (i) of isolating the compound of the Formula VI. The step (i) may comprise any suitable steps or procedures for isolating the desired product that are described in the literature and/or that are known to the skilled person. Particular steps that would be of use would provide high quality and high purity product. The reaction mixture may be cooled to ambient temperature, at which temperature the compound of the Formula VI typically forms a solid, and the solid so formed may be collected by any conventional method, for example by filtration.

Both the compound of the Formula VII and the 4-bromo-2-fluoroaniline starting material are commercially available or can be prepared using conventional methods. For example the compound of Formula VII, wherein $R^1$ is benzyl, may be prepared as described in example 2 below, preparation of starting materials.

Another key intermediate that may be used in the preparation of ZD6474 is 7-hydroxy-4-(4-bromo-2-fluoroanilino)-6-methoxyquinazoline, the compound of the Formula IX:

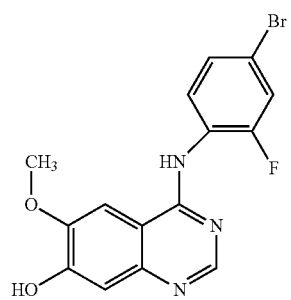

Example 2 of WO 01/32651 and Example 24 of WO 97/32856 each disclose a route for the preparation of a hydrochloride salt of a compound of the Formula IX. The route involves the reaction of a hydrochloride salt of 7-benzyloxy-4-(4-bromo-2-fluoroanilino)-6-methoxyquinazoline with trifluoroacetic acid to provide the compound of the Formula IX.

As discussed above, WO 98/10767 discloses a route for the preparation of 6,7-disubstituted 4-anilinoquinazoline compounds. There is no disclosure in WO 98/10767 of 7-hydroxy-4-(4-bromo-2-fluoroanilino)-6-methoxyquinazoline or of a process for its preparation.

The routes disclosed in the prior art documents for the preparation of a compound of the Formula IX are satisfactory for the synthesis of relatively small amounts of the compound. However, they all require the isolation and/or purification of intermediate compounds. This results in a satisfactory, but not high, overall yield of the compound of the Formula IX.

There is, therefore, a need for a more efficient synthesis of the compound of the Formula IX suitable for use to make larger quantities of that compound. Preferably, the new synthesis should not involve costly and time-consuming purification procedures. Thus, the new synthesis should reduce the number of isolation and/or purification procedures required, thereby reducing costs and time of manufacture. Preferably, the new synthesis should minimise the number of solvents used throughout the process, which improves environmental performance and provides the opportunity for solvent recovery. The new synthesis should also enable effective crystallisation of the compound of the Formula IX in a crystalline form with good filtration characteristics and in high purity and yield.

According to a third aspect of the present invention, there is provided a process for the manufacture of 7-hydroxy-4-(4-bromo-2-fluoroanilino)-6-methoxyquinazoline, a compound of the Formula IX:

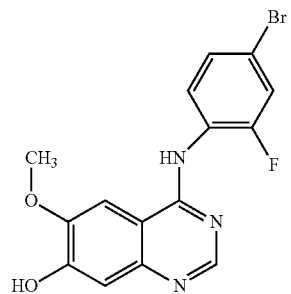

from a compound of the Formula VII:

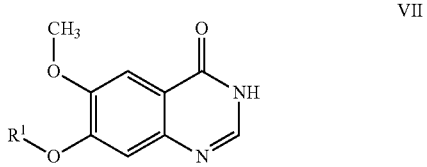

which process comprises the steps of:
(g) reacting the compound of the Formula VII with a suitable chlorinating agent in the presence of a suitable base and a suitable solvent, wherein the reaction is carried out by:
  (g-1) adding a mixture of the compound of the Formula VII and the base in the solvent to a mixture of the chlorinating agent in the solvent at a temperature in the range of from 60 to 110° C., conveniently 60 to 80° C. over a period of about 60 minutes; or
  (g-2) adding the chlorinating agent to a mixture of the compound of the Formula VII and the base in the solvent at ambient temperature over a period of about 15 minutes and then heating the reaction mixture over a period of about 90 minutes to a temperature in the range of from 70 to 90° C. and stirring the reaction mixture at that temperature for about 1 hour; or
  (g-3) adding the chlorinating agent to a mixture of the compound of the Formula VII and the base in the solvent at a temperature in the range of from 60 to 110° C., conveniently 70 to 90° C. over a period of about 15 minutes,
to form a compound of the Formula VIII:

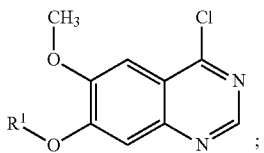

(h) reacting the compound of the Formula VIII with 4-bromo-2-fluoroaniline in situ in the presence of the solvent used in step (g) to form a compound of the Formula VI;

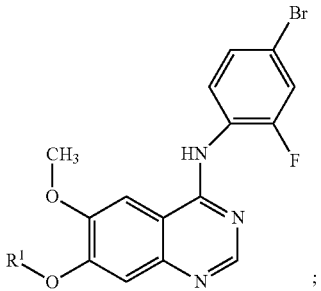

and
(j) removing $R^1$ from the compound of the Formula VI in situ in the presence of the solvent used in steps (g) and (h) to form the compound of the Formula IX or a salt thereof;
and whereafter the compound of the Formula IX obtained in the form of the free base may be converted into a salt form and the compound of the Formula IX obtained in the form of a salt may be converted into the free base or into the form of an alternative salt, if necessary.

The process of the third aspect of the invention is advantageous in that it allows the compound of the Formula IX to be made in high purity and high yield on a larger scale. Typically, each of the steps of the process of the third aspect of the present invention proceeds in at least 95% yield. Typically, the process of the third aspect of the present invention produces the compound of the Formula IX in at least 85% yield.

Steps (g), (h) and (j) are all conducted in the same solvent, which solvent is selected from an aryl alkyl ether, such as anisole, a dialkyl ether such as 1,2-dimethyl ether, a halo substituted benzene such as chlorobenezene or trifluorotoluene or an alkyl substituted benzene such as xylene, ethyl benzene or toluene. In one embodiment of the invention the solvent for step (g), (h) and (j) is anisole or toluene. In another embodiment of the invention the solvent for step (g), (h) and (j) is toluene. This allows the process to be conducted as a continuous process without isolation and/or purification of the intermediate compounds of the Formulae VIII and VI. This significantly reduces the time and cost of manufacturing the compound of the Formula IX on a larger scale. The use of a single solvent may allow for solvent recycling, which increases the efficiency of the process and provides environmental benefits. The use of these solvents as the reaction solvent is advantageous because these solvents minimise the formation of by-products that may be derived by dimerisation of the compound of the Formula VII, as discussed above. The choice of solvent also allows for the easy and convenient isolation of the compound of the Formula VI. For example, when the reaction mixture is cooled to ambient temperature, the compound of the Formula VI typically forms a solid, which may then be collected by any conventional method.

As discussed above, the mode of addition of the reagents in step (g) (i.e. as described in steps (g-1), (g-2) and (g-3)) is advantageous because it minimises the formation of by-products/impurities in that step (which by-products/impurities typically are predominantly formed by dimerisation of the compound of the Formula VII). This enables the intermediate compound of the Formula VIII produced in step (g) to be used in step (h) without isolation and/or purification. Reducing the formation of by-products/impurities in step (g) allows for the correct stoichiometry of the reagents in step (h) of the process and, therefore, a more efficient reaction in that step. This is turn provides a high yield and high purity of the compound of the Formula VI in step (h).

In one aspect of the invention, steps (g), (h) and (j) are all conducted in toluene as the solvent. The use of toluene as the solvent in step (j) wherein R' is benzyl is advantageous because the toluene acts to capture the benzyl cation that is generated during the deprotection reaction. This aids in the reducing the benzylated impurities that potentially may be formed in step (j) of the process. Toluene also provides a more robust crystallisation of compound IX and a crystalline form of compound IX with superior filtration characteristics.

In another aspect of the invention, steps (g), (h) and (j) are all conducted in a single solvent such as anisole chlorobenezene, trifluorotoluene, xylene or ethyl benzene.

A suitable chlorinating agent for use in step (g) is phosphorus oxychloride. Typically, in step (g), a molar excess of chlorinating agent is used relative to the compound of the Formula VII. For example, a molar excess in the range of from 1.3 to 2.0, conveniently in the range of from 1.7 to 1.8, may be used.

A suitable base for use in step (g) is a base selected from triethylamine, tripropylamine and N,N-diisopropylethylamine. In particular, the base is triethylamine. The use of triethylamine as the base in step (g) is advantageous as it enables a more robust crystallisation of compound IX and a crystalline form of compound IX with superior filtration characteristics.

In step (g-1), the reaction is carried out at a temperature in the range of from 60 to 110° C., conveniently 60 to 80° C., conveniently in the range of from 65 to 75° C., more conveniently in the range of from 70 to 75° C.

In step (g-2), the addition of reagents is carried out at ambient temperature. By the term "ambient temperature" we mean a temperature in the range of from 10 to 30° C., especially a temperature in the range of from 15 to 25° C., more especially a temperature of about 20° C. The reaction mixture is then heated to a temperature in the range of from 70 to 90° C., conveniently in the range of from 75 to 85° C., more conveniently in the range of from 80 to 85° C.

In step (g-3), the reaction is carried out at a temperature in the range of from 60 to 110° C., conveniently 70 to 90° C., conveniently in the range of from 75 to 85° C., more conveniently in the range of from 80 to 85° C.

In step (g), the term "of about" is used in the expressions "of about 60 minutes", "of about 15 minutes", "of about 90 minutes and "of about 1 hour" to indicate that the time periods quoted should not be construed as being absolute values because, as will be appreciated by those skilled in the art, the time periods may vary slightly. For example, the time periods quoted may vary by ±50%, particularly ±15%, particularly by ±10% from the values quoted in step (g).

As the skilled person would appreciate, in step (g), the mixture of the compound of the Formula VII and the base in a suitable solvent will typically take the form of a suspension. The mixture of the chlorinating agent in a solvent selected from toluene and anisole will typically take the form of a solution. However, a number of factors may cause these forms to vary. Such factors may, for example, include the amount of each of the reagents added to the solvent and the particular base or chlorinating agent selected for use in step (g).

The reaction of step (h) is carried out at a temperature in the range of from 60 to 90° C., conveniently 60 to 85° C., conveniently in the range of from 65 to 80° C., more conveniently in the range of from 70 to 75° C.

In this aspect of the invention, following the manufacture of the compound of the Formula VI in step (h), the compound is used directly in step (j) for manufacturing a compound of the Formula IX. In other words, the compound of the Formula VI is not isolated as such but is used as a solution or slurry in a solvent selected from an aryl alkyl ether, such as anisole, a dialkyl ether such as 1,2-dimethoxyethane, a halo substituted benzene such as chlorobenzene or trifluorotoluene or an alkyl substituted benzene such as xylene, ethyl benzene or toluene. In one embodiment of the invention the solvent for step (j) is anisole or toluene. In another embodiment of the invention the solvent for step (j) is toluene. Thereby, the compound of the Formula IX may be manufactured from a compound of the Formula VII in a one-pot procedure.

A suitable method of removing the acid labile protecting group in situ in step (j) is by reaction with an acid, such as trifluoroacetic acid. Optionally, a second acid (such as hydrogen chloride or hydrogen bromide) may be used in addition to, or as a replacement for, the trifluoroacetic acid. When an acid is used to remove $R^1$ in step (j), then the compound of the Formula IX is obtained in the form of a salt. The use of trifluoroacetic acid in step (j) is advantageous because it allows for easy isolation of the compound of the Formula IX, for example by crystallisation from the trifluoroacetic acid by addition of water and cooling or by addition of and aqueous alkali metal base such as potassium hydroxide, sodium hydroxide, sodium acetate, potassium acetate, more preferably potassium hydroxide followed by water and cooling. The crystalline solid so formed may be collected by any conventional method, for example by filtration.

The reaction of step (j) is carried out at a temperature in the range of from 60 to 90° C., conveniently 60 to 80° C., more conveniently in the range of from 70 to 75° C.

In one aspect of the invention, following step (j) of the process, the compound of the Formula IX is isolated and/or purified. Any suitable steps or procedures for isolating and/or purifying the desired product that are described in the literature and/or that are known to the skilled person may be used. Particular steps that would be of use would provide high quality and high purity product. For example, the compound of the Formula IX may be isolated from trifluoroacetic acid by addition of water and cooling or more preferably by addition of and aqueous alkali metal base such as potassium hydroxide and water and cooling, as discussed above.

According to a fourth aspect of the present invention, there is provided a process for the manufacture of 7-hydroxy-4-(4-bromo-2-fluoroanilino)-6-methoxyquinazoline, a compound of the Formula IX:

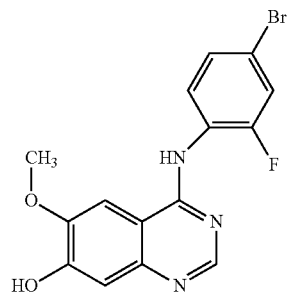

IX from a compound of the Formula VII:

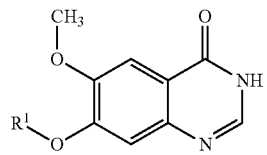

VII which process comprises the steps of:
(g) reacting the compound of the Formula VII with a suitable chlorinating agent in the presence of a suitable base and a suitable solvent selected from toluene and anisole, wherein the reaction is carried out by:
(g-1) adding a mixture of the compound of the Formula VII and the base in the solvent to a mixture of the chlorinating agent in the solvent at a temperature in the range of from 60 to 110° C., conveniently 60 to 80° C. over a period of about 60 minutes; or (g-2) adding the chlorinating agent to a mixture of the compound of the Formula VII and the base in the solvent at ambient temperature over a period of about 15 minutes and then heating the reaction mixture over a period of about 90 minutes to a temperature in the range of from 70 to 90° C. and stirring the reaction mixture at that temperature for about 1 hour; or (g-3) adding the chlorinating agent to a mixture of the compound of the Formula VII and the base in the solvent at a temperature in the range of from 60 to 110° C., conveniently 70 to 90° C. over a period of about 15 minutes, to form a compound of the Formula VIII:

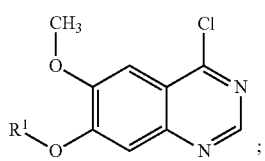

VIII (h) reacting the compound of the Formula VIII with 4-bromo-2-fluoro aniline in situ in the presence of the solvent used in step (g) to form the compound of the Formula VI:

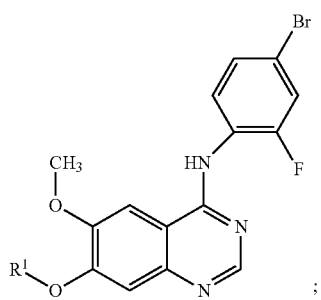

VI (i) isolating the compound of the Formula VI; and (k) removing $R^1$ from the compound of the Formula VI to form the compound of the Formula IX or a salt thereof;

and whereafter the compound of the Formula IX obtained in the form of the free base may be converted into a salt form and the compound of the Formula IX obtained in the form of a salt may be converted into the free base or into the form of an alternative salt such a trifluoroacetic acid or hydrochloride salt, if necessary.

The process of the fourth aspect of the invention is advantageous in that it allows a compound of the Formula IX to be made in high purity and high yield on a larger scale.

Steps (g) and (h) are both conducted in the same solvent, which solvent is selected from an aryl alkyl ether, such as anisole, a dialkyl ether such as 1,2-dimethyl ether, a halo substituted benzene such as chlorobenezene or trifluorotoluene or an alkyl substituted benzene such as xylene, ethyl benzene or toluene. In one embodiment of the invention the solvent for step (g) and (h) is anisole or toluene. In another embodiment of the invention the solvent for step (g) and (h) is toluene. This allows the process to be conducted as a continuous process without isolation and/or purification of the intermediate compound of the Formula VIII. This significantly reduces the time and cost of manufacturing the compound of the Formula IX on a larger scale. The use of a single solvent in steps (g) and (h) may allow for solvent recycling, which increases the efficiency of the process and provides environmental benefits. The use of toluene or anisole as the reaction solvent in steps (g) and (h) is advantageous because these solvents minimise the formation of by-products that may be derived by dimerisation of the compound of the Formula VII, as discussed above. The choice of solvent also allows for the easy and convenient isolation of the compound of the Formula VI. For example, when the reaction mixture is cooled to ambient temperature, the compound of the Formula VI typically forms a solid, which solid may then be collected by any conventional method.

As discussed above, the mode of addition of the reagents in step (g) (i.e. as described in steps (g-1), (g-2) and (g-3)) is advantageous because it minimises the formation of by-products/impurities in that step (which by-products/impurities typically are predominantly formed by dimerisation of the compound of the Formula VII). This enables the intermediate compound of the Formula VIII produced in step (g) to be used in step (h) without isolation and/or purification. Reducing the formation of by-products/impurities in step (g) allows for the correct stoichiometry of the reagents in step (h) of the process and, therefore, a more efficient reaction in that step. This is turn provides a high yield and purity of the compound of the Formula VI in step (h).

In one aspect of the invention, steps (g) and (h) are both conducted in toluene as the solvent. In another aspect of the invention, steps (g) and (h) are both conducted in anisole as the solvent.

A suitable chlorinating agent for use in step (g) is phosphorus oxychloride. Typically, in step (g), a molar excess of chlorinating agent is used relative to the compound of the Formula VII. For example, a molar excess in the range of from 1.3 to 2.0, conveniently in the range of from 1.7 to 1.8, may be used.

A suitable base for use in step (g) is a base selected from triethylamine and N,N-diisopropylethylamine. In one embodiment, the base is triethylamine. The use of triethylamine as the base in step (g) is advantageous as it enables a more robust crystallisation of compound IX and a crystalline form of compound IX with superior filtration characteristics.

In another embodiment, the base is N,N-diisopropylethylamine. The use of N,N-diisopropylethylamine as the base in step (g) is advantageous because it minimises the formation of by-products that may be derived by dimerisation of the compound of the Formula VII, as discussed above (for example as compared to the use of triethylamine as the base in step (g)). Adding a source of chloride to the reaction mixture (such as, for example, triethylamine hydrochloride) may also reduce the formation of such by-products.

In step (g-1), the reaction is carried out at a temperature in the range of from 60 to 110° C., conveniently 60 to 80° C., conveniently in the range of from 65 to 75° C., more conveniently in the range of from 70 to 75° C.

In step (g-2), the addition of reagents is carried out at ambient temperature. By the term "ambient temperature" we mean a temperature in the range of from 10 to 30° C., especially a temperature in the range of from 15 to 25° C., more especially a temperature of about 20° C. The reaction mixture is then heated to a temperature in the range of from 70 to 90° C., conveniently in the range of from 75 to 85° C., more conveniently in the range of from 80 to 85° C.

In step (g-3), the reaction is carried out at a temperature in the range of from 60 to 110° C., conveniently 70 to 90° C., conveniently in the range of from 75 to 85° C., more conveniently in the range of from 80 to 85° C.

In step (g), the term "of about" is used in the expressions "of about 60 minutes", "of about 15 minutes", "of about 90 minutes and "of about 1 hour" to indicate that the time periods quoted should not be construed as being absolute values because, as will be appreciated by those skilled in the art, the time periods may vary slightly. For example, the time periods quoted may vary by ±50%, particularly ±15%, particularly by ±10% from the values quoted in step (g).

As the skilled person would appreciate, in step (g), the mixture of the compound of the Formula VII and the base in a suitable solvent will typically take the form of a suspension. The mixture of the chlorinating agent in a solvent selected from toluene and anisole will typically take the form of a solution. However, a number of factors may cause these forms to vary. Such factors may, for example, include the amount of each of the reagents added to the solvent and the particular base or chlorinating agent selected for use in step (g).

The reaction of step (h) is carried out at a temperature in the range of from 60 to 90° C., conveniently 60 to 90° C., conveniently in the range of from 65 to 80° C., more conveniently in the range of from 70 to 75° C.

In this aspect of the invention, following the manufacture of the compound of the Formula VI in step (h), the compound is isolated and, optionally, purified in step (i) of the process. The isolated compound of the Formula VI is then used in step (k) for manufacturing a compound of the Formula IX, either immediately or following storage for an appropriate period of time. The isolation of the compound of the Formula VI in step (i) wherein R$^1$ is benzyl is advantageous because it enables a broader choice of methods for removing the benzyl group from the compound of the Formula VI in step (k), for example compared to when this step is conducted in situ.

The step (k) wherein R$^1$ is benzyl may comprise any suitable steps or procedures for removing the benzyl group that are described in the literature and/or that are known to the skilled person. Particular steps that would be of use would provide high quality and high purity product. For example, in step (k) the benzyl may be removed by reaction with a suitable hydrogenation agent, such as palladium on carbon, for example in the presence of a suitable moderating agent, such as zinc bromide or zinc iodide. The use of a hydrogenation agent is advantageous because it provides a highly efficient method of removing the benzyl group in step (k) and because it allows for the efficient removal of by-products from the waste stream.

A further suitable method of removing the acid labile protecting group wherein R$^1$ is a benzyl group in step (k) is by reaction with an acid, such as trifluoro acetic acid. Optionally, a second acid (such as hydrogen chloride or hydrogen bromide) may be used in addition to, or as a replacement for, the trifluoroacetic acid. When an acid is used to remove the benzyl group in step (k), then the compound of the Formula IX is obtained in the form of a salt. The use of trifluoroacetic acid in step (k) is advantageous because it allows for easy isolation of the compound of the Formula IX, for example by crystallisation from the trifluoroacetic acid by addition of water and cooling or more preferably by addition of an aqueous alkali metal base such as potassium hydroxide, sodium hydroxide, sodium acetate, potassium acetate, more preferably potassium hydroxide followed by water and cooling. The crystalline solid so formed may be collected by any conventional method, for example by filtration.

The reaction of step (k) wherein R$^1$ is benzyl may be carried out at any temperature and in any solvent suitable for the particular method of removal of the benzyl group being used. Examples of suitable solvents fore acid-based removal of the benzyl group include ethanol, an aryl alkyl ether, such as anisole, a dialkyl ether such as 1,2-dimethyl ether, a halo substituted benzene such as chlorobenezene or trifluorotoluene or an alkyl substituted benzene such as xylene, ethyl benzene or toluene or dichloromethane.

In one aspect of the invention, following step (k) of the process, the compound of the Formula IX is isolated and/or purified. Any suitable steps or procedures for isolating and/or purifying the desired product that are described in the literature and/or that are known to the skilled person may be used. Particular steps that would be of use would provide high quality and high purity product.

Another key intermediate that may be used in the preparation of ZD6474 is 7-(1-tert-butoxycarbonyl)piperidine-4-ylmethoxy)-4-(4-bromo-2-fluoroanilino)-6-methoxyquinazoline, the compound of the Formula X:

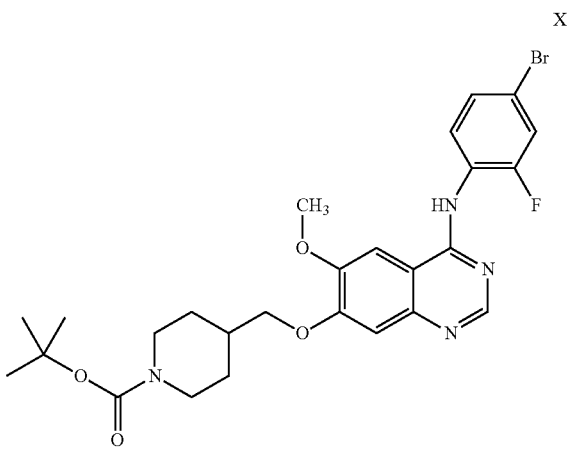 [SMILES: COc1cc2c(Nc3ccc(Br)cc3F)ncnc2cc1OCC1CCN(C(=O)OC(C)(C)C)CC1]

Example 2 of WO 01/32651 discloses a route for the preparation of a compound of the Formula X. The route involves the reaction of 7-hydroxy-4-(4-bromo-2-fluoroanilino)-6-methoxyquinazoline with potassium carbonate and 1-(tert-butoxycarbonyl)-4-(4-methylphenylsulfonyloxymethyl)piperidine in a N,N-dimethylformamide solvent to provide the compound of the Formula X.

As discussed above, WO 98/10767 discloses a route for the preparation of 6,7-disubstituted 4-anilinoquinazoline compounds. There is no disclosure in WO 98/10767 of 7-(1-tert-butoxycarbonyl)piperidine-4-ylmethoxy)-4-(4-bromo-2-fluoroanilino)-6-methoxyquinazoline or of a process for its preparation.

The routes disclosed in the prior art documents for the preparation of a compound of the Formula X are satisfactory for the synthesis of relatively small amounts of the compound. However, there is a need for a more efficient synthesis of the compound of the Formula X suitable for use to make larger quantities of that compound. Preferably, the new synthesis should not involve costly and time-consuming purification procedures. Thus, the new synthesis should reduce the number of isolation and/or purification procedures required, thereby reducing costs and time of manufacture. Preferably, the new synthesis should minimise the number of solvents used throughout the process, which improves environmental performance and provides the opportunity for solvent recovery. The new synthesis should also provide the compound of the Formula X in a high purity and in a high yield.

According to a fifth aspect of the present invention, there is provided a process for the manufacture of 7-(1-tert-butoxycarbonyl)piperidine-4-ylmethoxy)-4-(4-bromo-2-fluoroanilino)-6-methoxyquinazoline, a compound of the Formula X:

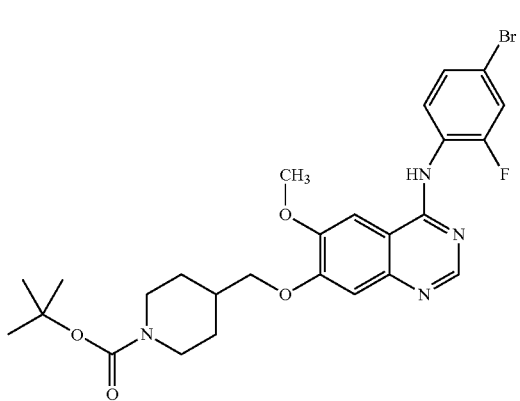

from a compound of the Formula VII:

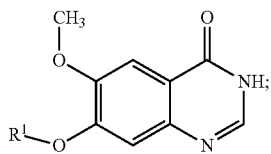

which process comprises the steps of converting the compound of the Formula VII to a compound of the Formula IX:

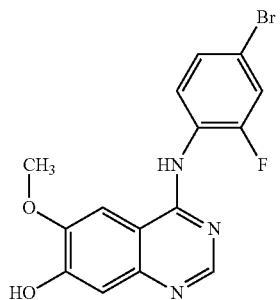

by conducting a process as discussed above in relation to the third or the fourth aspect of the invention; and
(l) reacting the compound of the Formula IX with a compound of the Formula II as defined above in the presence of a suitable base to provide a compound of the Formula X or a salt thereof;
and whereafter the compound of the Formula X obtained in the form of the free base in either solvated or non-solvated forms may be converted into a salt form and the compound of the Formula X obtained in the form of a salt may be converted into the free base or into the form of an alternative salt, if necessary.

The process of the fifth aspect of the invention is advantageous in that it allows the compound of the Formula X to be made in high purity and high yield on a larger scale. Typically the process of the fifth aspect of the present invention proceeds in greater than 80% yield. The process of the fifth aspect of the invention is also advantageous for at least the reasons discussed above in relation to the third and fourth aspects of the invention.

Typically, the compound of the Formula IX is isolated and/or purified before step (l) is conducted, for example using any suitable steps or procedures that are described in the literature and/or that are known to the skilled person as discussed above.

In another embodiment of the invention following the manufacture of the compound of the Formula IX in step (j) wherein $R^1$ is benzyl (or substituted benzyl) and when hydrogenation is used as the method of deprotection of the benzyl group, the compound is used directly in step (l) for manufacturing a compound of the Formula X. In other words, the compound of the Formula IX is not isolated as such but is used as a solution or slurry in a suitable solvent such as N-methyl pyrrolidone, dimethylformamide or dimethylacetamide. In one embodiment of the invention the solvent for step (j) is N-methylpyrolidone. Thereby, the compound of the Formula X may be manufactured from a compound of the Formula VIII in a one-pot procedure.

A suitable base for use in step (l) is selected from sodium carbonate, sodium bicarbonate, potassium carbonate, sodium hydroxide, potassium tert-butanol, and potassium hydroxide.

Step (l) may be conducted in any suitable solvent and at any suitable temperature.

When the base used in step (l) is selected from sodium carbonate and potassium carbonate, suitable solvents include, for example, N-methylpyrrolidone, N-ethylpyrrolidone, dimetylacetamide, dimethylsulphoxide, sulpholine, methylethyl ketone and N,N-dimethylformamide. In this aspect, step (l) typically may be conducted at a temperature in the range of from 60 to 120° C., conveniently 70 to 105° C., conveniently in the range of from 80 to 100° C., conveniently in the range 70-90° C., conveniently in the range of from 90 to 95° C. In a further embodiment in the range 75-85° C.

When the base used in step (l) is selected from sodium hydroxide and potassium hydroxide, suitable solvents include, for example, an aryl alkyl ether, such as anisole, a dialkyl ether such as 1,2-dimethoxyethane, a halo substituted benzene such as chlorobenezene or trifluorotoluene or an alkyl substituted benzene such as xylene, ethyl benzene or toluene or acetonitrile. In one embodiment of the invention the solvent for step (l) is anisole or toluene. In another embodiment of the invention the solvent for step (l) is toluene. In this aspect, step (l) typically may be conducted at a temperature in the range of from 60 to 90° C., conveniently in the range of from 65 to 85° C., conveniently in the range of from 70 to 80° C. In this aspect, step (l) may conveniently be conducted by adding water, the base (such as sodium hydroxide or potassium hydroxide) and a suitable phase transfer catalyst in toluene to the reaction mixture. Suitable phase transfer catalysts include, for example, tetrabutylammonium bromide and Adogen® 464 (methyltrialkyl($C_{8-10}$) ammonium chloride, CAS 63393-96-4).

In one aspect, the process of the fifth aspect of the invention may include the step (m) of isolating the compound of the Formula X. The step (m) may comprise any suitable steps or procedures for isolating the compound of the Formula X that are described in the literature and/or that are known to the skilled person.

For example, when the base used in step (l) is selected from sodium carbonate and potassium carbonate, step (m) may comprise the steps of:

(m-1) adding water and allowing crystallisation of the compound of the Formula X to occur, collecting the compound of the Formula X and washing the compound of the Formula X with water, followed by a solvent selected from ethyl acetate, butyl acetate and acetonitrile at a temperature in the range of from 25 to 55° C., conveniently from 45 to 55° C.; or (m-2) adding water and an alcohol selected from methanol, ethanol, isopropanol and n-propanol (particularly isopropanol) and allowing crystallisation of the compound of the Formula X to occur, collecting the compound of the Formula X and washing the compound of the Formula X with a mixture of water and the alcohol selected from selected from methanol, ethanol, isopropanol and n-propanol, followed by a solvent selected from ethyl acetate, butyl acetate and acetonitrile at a temperature in the range of from 25 to 55° C., conveniently from 45 to 55° C.

The steps (m-1) and (m-2) are advantageous because they are efficient at removing unreacted compound of the Formula IX, as well as impurities that are routinely formed during step (l) of the process. Such impurities include those formed by reaction of the compound of the Formula II at the 1-position nitrogen atom in the quinazoline ring instead of at the desired position at the hydroxy substituent.

When the base used in step (l) is selected from sodium hydroxide and potassium hydroxide, step (in) may comprise the steps of allowing crystallisation of the compound of the Formula X to occur (for example to crystallise from the toluene phase) and collecting the compound of the Formula X by any conventional method. This aspect is advantageous because the compound of the Formula X crystallises directly from the reaction mixture in high yield (for example at least 80% yield) and in high quality without the need to further purify the product.

In steps (m), the compound of the Formula X so formed (for example which is isolated as a crystalline solid) may be collected by any conventional method, for example by filtration. The collected crystalline solid may, if necessary, then be washed with the appropriate solvent and may then be dried.

According to a sixth aspect of the present invention, there is provided a process for the manufacture of 7-(1-tert-butoxycarbonyl)piperidine-4-ylmethoxy)-4-(4-bromo-2-fluoroanilino)-6-methoxyquinazoline, a compound of the Formula X:

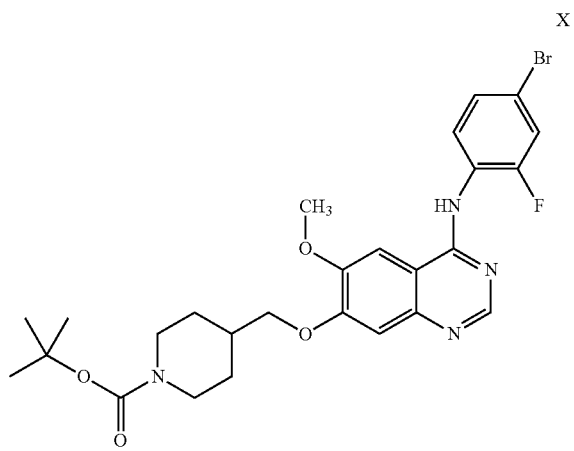 [SMILES: COc1cc2c(Nc3ccc(Br)cc3F)ncnc2cc1OCC1CCN(C(=O)OC(C)(C)C)CC1]

from 7-hydroxy-4-(4-bromo-2-fluoroanilino)-6-methoxyquinazoline, a compound of the Formula IX:

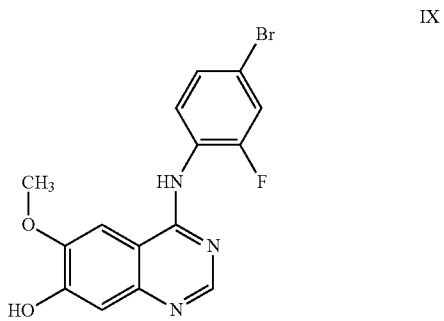 [SMILES: COc1cc2c(Nc3ccc(Br)cc3F)ncnc2cc1O]

(l) reacting the compound of the Formula IX with a compound of the Formula II as defined above in the presence of a suitable base to provide a compound of the Formula X or a salt thereof; and (m) isolating the compound of the Formula X by:

(m-1) adding water and allowing crystallisation of the compound of the Formula X to occur, collecting the compound of the Formula X and washing the compound of the Formula X with water, followed by a solvent selected from ethyl acetate, butyl acetate and acetonitrile at a temperature in the range of from 25 to 55° C., conveniently 45 to 55° C.; or (m-2) adding water and an alcohol selected from methanol, ethanol, isopropanol and n-propanol (particularly isopropanol) and allowing crystallisation of the compound of the Formula X to occur, collecting the compound of the Formula X and washing the compound of the Formula X with a mixture of water and the alcohol selected from methanol, ethanol, isopropanol and n-propanol, followed by a solvent selected from ethyl acetate, butyl acetate and acetonitrile at a temperature in the range of from 25 to 55° C., conveniently 25 to 55° C.;

and whereafter the compound of the Formula X obtained in the form of the free base in either solvated or non solvated forms (or solvate of solvents from NMP, Ethyl Acetate or a mixture of both) may be converted into a salt form and the compound of the Formula X obtained in the form of a salt may be converted into the free base or into the form of an alternative salt, if necessary.

The process of the sixth aspect of the invention is advantageous in that it allows the compound of the Formula X to be made in high purity and high yield on a larger scale. Typically, each of the steps of the process of the sixth aspect of the present invention proceeds in greater than 80% yield.

The process provides for the efficient removal of any unreacted compound of the Formula IX, as well as of any impurities that are routinely formed during step (l) of the process. Such impurities include those formed by reaction of the compound of the Formula II at the 1-position nitrogen atom in the quinazoline ring instead of at the desired position at the hydroxy substituent.

A suitable base for use in step (l) is selected from sodium carbonate, sodium hydroxide, potassium hydroxide and potassium carbonate.

Step (l) may be conducted in any suitable solvent or at any suitable temperature.

When the base used in step (l) is selected from sodium carbonate and potassium carbonate, suitable solvents include, for example, N-methylpyrrolidone, N-ethylpyrrolidone and N,N-dimethylformamide. In this aspect, step (l) typically may be conducted at a temperature in the range of from 70 to 105° C., conveniently of from 80 to 100° C., conveniently of from 90 to 95° C.

The steps (m-1) and (m-2) are advantageous because they are efficient at removing unreacted compound of the Formula IX, as well as impurities that are routinely formed during step (l) of the process. Such impurities include those formed by reaction of the compound of the Formula II at the 1-position nitrogen atom in the quinazoline ring instead of at the desired position at the hydroxy substituent.

In steps (m-1) and (m-2), the crystalline solid so formed may be collected by any conventional method, for example by filtration. The collected crystalline solid may, if necessary, then be washed with the appropriate solvent and may then be dried.

The compound of the Formula II used in step (l) of the processes of the fifth and sixth aspects of the invention may be obtained by any literature or conventional method. In one aspect of the invention, the compound of the Formula II used in step (l) of the fifth or sixth aspect of the invention is prepared according to the process of the first aspect of the invention, as discussed above.

According to a seventh aspect of the invention, there is provided a process for the manufacture of ZD6474:

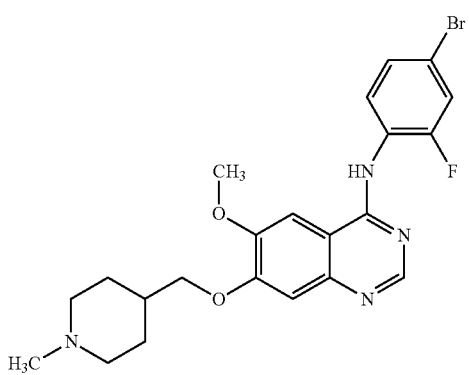

ZD6474 from a compound of the Formula X:

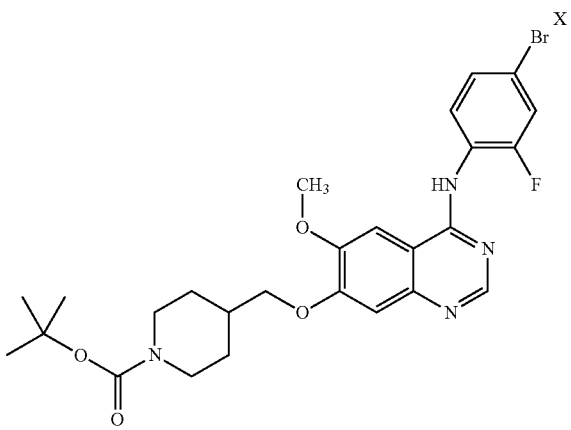 [SMILES: COc1cc2c(Nc3ccc(Br)cc3F)ncnc2cc1OCC1CCN(C(=O)OC(C)(C)C)CC1]

X which process comprises the steps of:
(n) reacting the compound of the Formula X with formic acid and formaldehyde or a polymer of formaldehyde, conveniently in water at a temperature in the range of from 70 to 95° C., conveniently 70 to 90° C. to form a formic acid salt of ZD6474;
(o) adding an inert organic solvent selected from tetrahydrofuran, butyronitrile and methanol and a suitable base so as to form the free base of ZD6474;
whereafter the ZD6474 obtained in the form of the free base may be converted into a pharmaceutically acceptable salt, if necessary.

In step (n) of the process of the seventh aspect of the invention, the reaction proceeds via a transient intermediate, which intermediate is 4-(4-bromo-2-fluoroanilino)-6-methoxy-7-(piperidin-4-ylmethoxy)quinazoline, a compound of the Formula XI:

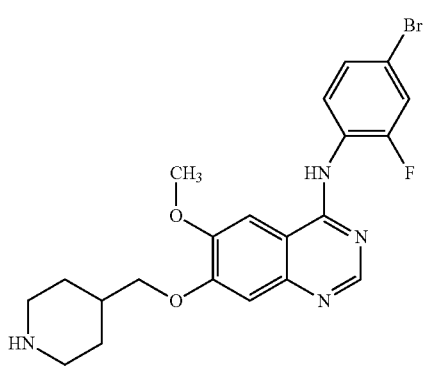

XI

The process of the seventh aspect of the invention is advantageous in that it allows the ZD6474 to be made in high purity and high yield on a larger scale. Typically, each of the steps of the process of the seventh aspect of the present invention proceeds in greater than 90% yield.

The compound of the Formula X used in step (n) of the process of the seventh aspect of the invention may be obtained by any literature or conventional method (for example, as described in WO 01/32651 discussed previously). Alternatively, in one aspect of the invention, the compound of the Formula X used in step (n) of the seventh aspect of the invention is prepared according to the process of the fifth or the sixth aspect of the invention, as discussed above.

Step (n) is conducted at a temperature in the range of from 70 to 95° C., conveniently 70 to 90° C., conveniently in the range of from 75 to 85° C., more conveniently at about 80° C.

Preferably, step (n) is conducted under an inert atmosphere, for example under a nitrogen atmosphere. This is advantageous because the process of step (n) may produce hydrogen gas and carbon monoxide as a by-product, which hydrogen gas must be removed from the reaction vessel in a safe and effective manner.

In step (n), the formic acid salt of ZD6474 is produced. This salt is converted to the free base of ZD6474 in step (o) of the process.

In step (n) examples of polymers of formaldehyde include paraformaldehyde and s-trioxane (1,3,5 trioxane).

A suitable inert organic solvent for use in step (o) is selected from tetrahydrofuran, butyronitrile and methanol (particularly tetrahydrofuran or methanol). The inert organic solvent is added to the reaction mixture after the completion of the reaction in step (n). As the skilled person would appreciate, it may be necessary to cool the reaction mixture before the inert organic solvent is added.

A suitable base for use in step (o) is sodium hydroxide or potassium hydroxide (particularly potassium hydroxide). The addition of a base in step (o) converts the formic acid salt of ZD6474 to the free base of ZD6474.

When the inert organic solvent used in step (o) is selected from tetrahydrofuran and butyronitrile, the ZD6474 product is effectively transferred from the aqueous phase to the organic phase. This is because, once made, the free base of ZD6474 is preferentially soluble in the inert organic solvent (whereas the formic acid salt of ZD6474 is soluble in the aqueous phase). When the inert organic solvent used in step (o) is methanol, the free base of ZD6474 typically crystallises directly from the reaction mixture. When the base is potassium hydroxide this is particularly advantageous as the formate salt are completely soluble in the methanol solvent and don't contaminate the isolated compound ZD6474. This also provide a crystalline compound with good filtration characteristics. (this can be isolated as either the anhydrate form, a methanoate form or a mixed methanoate hydrate). Thus, step (o) of the process is advantageous because it aids and simplifies the isolation and purification of the ZD6474 product, particularly when the process is conducted on a larger scale.

Step (o) is conducted at a temperature in the range of from 30 to 70° C., conveniently in the range of from 40 to 65° C., more conveniently in the range of from 40 to 60° C.

In one aspect, the process of the seventh aspect of the invention may include the step (p) of isolating and/or purifying the free base of the ZD6474. The step (p) may comprise any suitable steps or procedures for isolating and/or purifying the free base of ZD6474 that are described in the literature and/or that are known to the skilled person. Alternatively, for example, when the inert organic solvent used in step (o) is selected from tetrahydrofuran and butyronitrile, the step (p) may comprise the steps of (p-1) separating and removing the aqueous phase from the organic phase;

(p-2) charging n-butyl acetate to the organic phase;

(p-3) washing the organic phase with water and separating and removing the aqueous phase from the organic phase;

(p-4) adding tetrahydrofuran and n-butyl acetate to the organic phase;

(p-5) distilling the organic phase so as to substantially remove the water and the tetrahydrofuran and to provide a suspension of ZD6474 in predominately n-butyl acetate;

(p-6) allowing crystallisation of the ZD6474 to complete; and (p-7) collecting the ZD6474.

The steps (p-1), (p-2) and (p-3) are advantageous because they readily and easily remove formic acid salts and residual formaldehyde or polymer of formaldehyde from the ZD6474 product dissolved in the organic phase.

In one aspect, the steps (p-1), (p-2), (p-3) and (p-4) are each conducted at a temperature in the range of from 50 to 65° C., conveniently in the range of from 55 to 65° C., more conveniently of about 60° C.

Typically, steps (p-1), (p-2) and (p-3) may each be repeated twice before step (p-4) is conducted.

Step (p-5) substantially removes any water and tetrahydrofuran that is present in the organic phase that has been separated from the aqueous phase in steps (p-1) and (p-3). The distillation is conducted so as to provide a solvent composition that contains about 90% w/w n-butyl acetate. In other words, the solution of ZD6474 in predominantly n-butyl acetate is a solution of ZD6474 in a solvent composition that contains about 90% w/w n-butyl acetate. Typically, the distillation is conducted until an internal temperature in the range of from 90 to 110° C., conveniently 90 to 104° C. is achieved conveniently in the range of from 100-110° C. The distillation in step (p-5) is conveniently conducted at atmospheric pressure (or reduced pressure but more conveniently at ambient pressure).

For the avoidance of doubt in (p-6) where it refers to 'allowing crystallisation of the ZD6474 to complete' this means that the crystallisation process has completed at the conditions used, it does not mean that 100% of the ZD6474 in the reaction mixture has crystallised.

An alternative step (p) of isolating and/or purifying the free base of ZD6474, when the inert organic solvent used in step (o) is tetrahydrofuran, may comprise the steps of:

(p-8) adding water to the ZD6474 solution in the organic phase obtained after step (p-1) so as to allow crystallisation of the ZD6474 to occur; and (p-9) collecting the ZD6474.

In each of the above isolation steps, the crystalline solid so formed may be collected by any conventional method, for example by filtration. The collected crystalline solid may, if necessary, then be purified further, and may then be dried.

The step (p) of isolating the ZD6474 product is advantageous because it provides ZD6474 in a high yield (for example typically in greater than 90% yield) and a high purity (for example typically in greater than 99% purity). In addition, the step (p) provides a form of ZD6474 that is easily filterable on a larger scale.

In another aspect of the present invention, the ZD6474 prepared according to the process of the seventh aspect of the invention as discussed above may be further purified. The further purification of ZD6474 may comprise any suitable steps or procedures for isolating and/or purifying ZD6474 that are described in the literature and/or that are known to the skilled person. Alternatively, the further purification of the ZD6474 may comprise the steps of heating a suspension of the ZD6474 as prepared in the process of the seventh aspect of the present invention in a mixture of tetrahydrofuran, water and butyl acetate to reflux, cooling the resulting mixture to a temperature in the range of from 50 to 65° C. (conveniently of about 60° C.), separating the aqueous and organic phases and filtering the organic phase. The filtrate may then be combined with further tetrahydrofuran and butyl acetate and the resulting mixture heated to a temperature in the range of 90 to 110° C., conveniently 90 to 110° C. (conveniently in a range of from 100 to 110° C.) before being cooled to a temperature in the range of from 40 to −10° C., conveniently 25 to 0° C. (conveniently in the range of from 0 to 10° C., more conveniently of about 5° C., in a further embodiment at a temperature of about 25° C.) to provide a slurry of ZD6474. The ZD6474 may then be collected by any conventional method, for example by filtration, and optionally washed with ethyl acetate. This is advantageous because the described process reduces the level of water at the end of the distillation to below 1% thus ensuring that the anhydrrous form of ZD6474 is produced.

Alternatively, for example, when the inert organic solvent used in step (o) is tetrahydrofuran, the step (p) may comprise the steps of:

(p-1) separating and removing the aqueous phase from the organic phase;

(p-2) filtering the organic phase;

(p-3) charging n-butyl acetate to the organic phase;

(p-4) washing the organic phase with water and separating and removing the aqueous phase from the organic phase;

(p-5) adding tetrahydrofuran and n-butyl acetate to the organic phase;

(p-6) distilling the organic phase so as to substantially remove the water and the tetrahydrofuran and to provide a suspension of ZD6474 in predominately n-butyl acetate;

(p-7) cooling and charging additional tetrahydrofuran; and (p-8) allowing crystallisation of the ZD6474 to complete; and (p-9) collecting the ZD6474.

The step (p-7) is advantageous because it improves the quality of the product obtained by solubilising the impurities in the mother liquors. This allows the telescoping of the production of the Crude API (Active Pharmaceutical Ingredient) with the isolation of the purified API in a single step.

According to an eighth aspect of the present invention, there is provided a process for the manufacture of ZD6474 from a compound of the Formula VII:

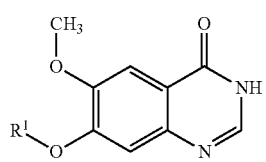

VII which process comprises the steps of:

(g) reacting the compound of the Formula VII with a suitable chlorinating agent in the presence of a suitable base and a solvent selected from chlorobenezene, trifluorotoluene, xylene, ethyl benzene, toluene & anisole more specifically anisole and toluene, wherein the reaction is carried out by:

(g-1) adding a mixture of the compound of the Formula VII and the base in the solvent to a mixture of the chlorinating agent in the solvent at a temperature in the range of from 60 to 90° C., conveniently 60 to 80° C. over a period of about 60 minutes; or (g-2) adding the chlorinating agent to a mixture of the compound of the Formula VII and the base in the solvent at ambient temperature over a period of about 15 minutes and then heating the reaction mixture over a period of about 90 minutes to a temperature in the range of from 70 to 90° C. and stirring the reaction mixture at that temperature for about 1 hour; or (g-3) adding the chlorinating agent to a mixture of the compound of the Formula VII and the base in the solvent at a temperature in the range of from 60 to 110° C., conveniently 70 to 90° C. over a period of about 15 minutes, to form a compound of the Formula VIII:

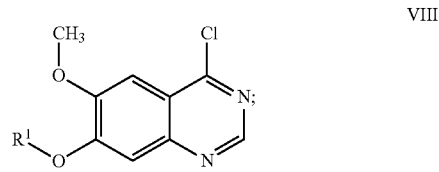

VIII (h) reacting the compound of the Formula VIII with 4-bromo-2-fluoroaniline in situ in the presence of the solvent used in step (g) to form a compound of the Formula VI:

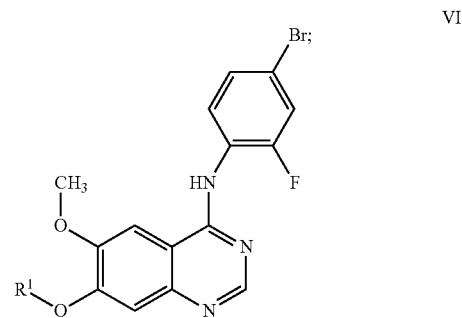

VI (j) removing $R^1$ from the compound of the Formula VI in situ in the presence of the solvent used in steps (g) and (h) to form the compound of the Formula IX:

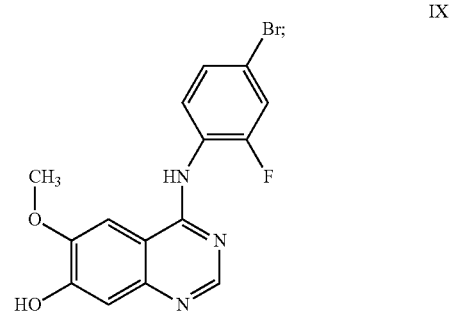 [SMILES: COc1cc2c(Nc3ccc(Br)cc3F)ncnc2cc1O]

IX (l) reacting the compound of the Formula IX with a compound of the Formula II as defined above in the presence of a suitable base to provide a compound of the Formula X;

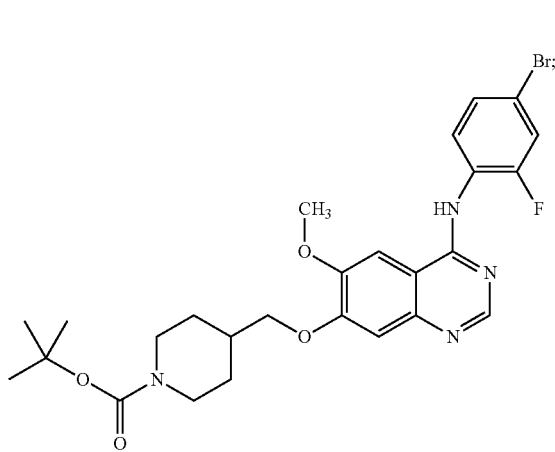

(n) reacting the compound of the Formula X with formic acid and formaldehyde or a polymer of formaldehyde conveniently in water at a temperature in the range of from 70 to 90° C. to form the formic acid salt of ZD6474; and
(o) adding an inert organic solvent selected from tetrahydrofuran, butyronitrile and methanol and a suitable base so as to form the free base of ZD6474; and optionally
(p) further purifying ZD6474 in a mixture of tetrahydrofuran, water and butyl acetate to provide a required crystalline anhydrous form suitable for tablet manufacture.

whereafter the ZD6474 obtained in the form of the free base may be converted into a pharmaceutically acceptable salt form, if necessary.

The process of the eighth aspect of the invention is advantageous in that it allows the ZD6474 to be made in high purity and high yield on a larger scale. Typically, each of the steps of the process of the seventh aspect of the present invention proceeds in greater than 90% yield.

Preferred aspects of the process of the eighth aspect of the invention are as set out above in relation to individual steps as described in the first, second, third, fourth, fifth, sixth and seventh aspects of the present invention. In particular, preferred aspects of the process of the eighth aspect of the invention are as set out above, for example, in relation to individual steps of the third, fifth, sixth and/or seventh aspects of the present invention.

Conveniently, steps (g), (h) and (j) of the process of the eighth aspect of the present invention are all conducted in toluene as the solvent and triethylamine as the base.

Conveniently, a suitable method of removing the benzyl group in situ in step (j) of the process of the eighth aspect of the present invention, wherein $R^1$ is benzyl, is by reaction with trifluoroacetic acid.

Conveniently, the base used in step (l) of the process of the eighth aspect of the present invention is potassium carbonate and the suitable solvent is N-methylpyrrolidone.

The process of the eighth aspect of the present invention typically may include the step (m) of isolating the compound of the Formula X before steps (n) and (o) are conducted. Conveniently, the step (m) may be conducted as hereinbefore described.

Conveniently, a suitable base for use in step (o) of the eighth aspect of the present invention is potassium hydroxide.

Conveniently, a suitable solvent for use in step (o) of the eighth aspect of the present invention is methanol.

The process of the eighth aspect of the present invention may include the step (p) of isolating and/or purifying the free base of the ZD6474. The step (p) may be conducted as hereinbefore described.

The invention is illustrated hereinafter by means of the following non-limiting Examples and Data in which, unless otherwise stated:—

(i) evaporations were carried out by rotary evaporation in vacuo and work-up procedures were carried out after removal of residual solids such as drying agents by filtration;

(ii) yields are given for illustration only and are not necessarily the maximum attainable;

(iii) melting points are uncorrected and were determined using a Mettler DSC820e;

(iv) the structures of the end-products were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet; quin, quintet; all samples run on a Bruker DPX 400 MHz at 300K in the solvent indicated, 16 scans, pulse repetition time 10 seconds;

(v) intermediates were not generally fully characterised and purity was assessed by NMR analysis;

(vi) chemical symbols have their usual meanings; SI units and symbols are used; and (vii) the following abbreviations have been used:—
THF tetrahydrofuran
IPA isopropanol
DMSO dimethylsulfoxide
TEDA triethylenediamine
DIPEA N,N-diisopropylethylamine
TFA trifluoroacetic acid
NMP N-methylpyrrolidinone
DMF N,N-dimethylformamide
DMA N,N-dimethylacetamide
v/v volume/volume ratio
w/w weight/weight ratio
w/v weight/volume ratio

EXAMPLE 1

Preparation of 1-(tert-butoxycarbonyl)-4-(4-methylphenylsulfonyloxymethyl)-piperidine (the Compound of the Formula II)

Di-tert-butyl dicarbonate (88.63 g) in toluene (296 ml) was added to a stirred solution of ethyl isonipecotate (62.88 g) in toluene (317 ml). The reaction mixture was then distilled at atmospheric pressure, removing about 130 ml of distillate, with a final distillation temperature of 112° C. Sodium bis(2-methoxyethoxy)aluminium hydride (Red-Al, 65% w/w solution in toluene, 161 g) in toluene (220 ml) was then added to the reaction mixture over a period of about 60 minutes. A solution of 0.5 molar Rochelle Salt (191 ml) was added to the reaction mixture and the aqueous phase was separated at 40° C. The organic phase was washed with 15% w/v brine (3×136 ml) and with water (136 ml). The solution was distilled at atmospheric temperature, removing about 400 ml of distillate, with a final distillation temperature of 112° C. Triethylenediamine (51.62 g) was added to the reaction mixture followed by tosyl chloride (87.90 g) in toluene (416 ml) over a period of about 60 minutes. Sodium hydroxide (2N, 160 ml) was added to the reaction mixture and the organic layer separated and washed successively with water (80 ml), citric acid (0.5M, 80 ml) and water (80 ml). The organic phase was concentrated at reduced pressure with a maximum internal temperature of 70° C., collecting about 600 ml of distillate. The solution was cooled to 20° C. and isohexane (160 ml) was added. Once crystallisation had occurred, further isohexane (320 ml) was added. The product was temperature cycled to 40° C., the suspension was cooled to 5° C. and the product was isolated by filtration and dried at 40° C. Yield: 127.9 g, 86.5%; NMR Spectrum (CDCl$_3$) 1.0-1.2 (m, 2H), 1.45 (s, 9H), 1.65 (d, 2H), 1.75-1.9 (m, 2H), 2.45 (s, 3H), 2.55-2.75 (m, 2H) 3.85 (d, 1H), 4.0-4.2 (br s, 2H), 7.35 (d, 2H), 7.8 (d, 2H); Mass Spectrum [ESI]: (MNa)$^+$=392.

EXAMPLE 2

Preparation of the hydrochloride salt of 7-benzyloxy-4-(4-bromo-2-fluoroanilino)-6-methoxyquinazoline (the Hydrochloride Salt of the Compound of the Formula VI)

7-Benzyloxy-6-methoxy-3,4-dihydroquinazolin-4-one (20.00 g) was mixed with anisole (190 ml) and N,N-diisopropylethylamine (13.74 g). The reaction mixture was inserted with nitrogen and cooled to 15° C. Phosphorus oxychloride (14.12 g) was charged to the reaction mixture over a period of 15 minutes followed by anisole (10 ml) as a wash. The reaction mixture was stirred for 15 minutes at 15° C. and then heated to 80° C. over a period of 90 minutes. The reaction mixture was then stirred at 80° C. for one hour. A solution of 4-bromo-2-fluoroaniline (16.8 g) in anisole (20 ml) was added to the reaction mixture over a period of 40 minutes. The reaction mixture was the stirred at 80° C. for 90 minutes. The reaction mixture was then cooled to 25° C. and the product isolated by filtration. Yield: 26.9 g, 84%; NMR Spectrum (DMSOd$_6$, CD$_3$COOD) 4.0 (s, 3H), 5.37 (s, 2H), 7.35-7.5 (m, 4H), 7.52-7.62 (m, 4H), 7.8 (d, 1H), 8.14 (s, 1H), 8.79 (s, 1H); Mass Spectrum [ESI] (M+H)$^+$=454.0591.

The 7-benzyloxy-6-methoxy-3,4-dihydroquinazolin-4-one starting material was prepared as follows:

A mixture of vanillic acid (200 g), acetonitrile (600 ml) and N-ethyldiisopropylamine (580 ml) was heated to reflux. Benzyl bromide (347 ml) was then added over a period of 3 hours. The reaction mixture was held at reflux for 15 hours. Triethylamine (50 ml) was added and the reaction mixture held at reflux for a further 30 minutes. Acetonitrile (400 ml) was added and the reaction mixture heated to 81° C. Water (300 ml) was added and the reaction mixture cooled to 45° C. The reaction mixture was held at 45° C. for 30 minutes until crystallisation occurred. The reaction mixture was then allowed to cool to 24° C. and then further cooled to 8° C. and the product (benzyl 4-(benzyloxy)-3-methoxybenzoate) isolated by filtration. The solid was washed with water (3×500 ml) and then dried under vacuum at 45° C. Yield: 387 g, 93.4%; NMR Spectrum (CDCl$_3$) 3.9 (s, 3H), 5.2 (s, 2H), 5.3 (s, 2H), 6.9 (d, 1H), 7.2-7.4 (m, 10H), 7.6-7.7 (m, 2H); Mass Spectrum (M+H)$^+$=349.2.

Benzyl 4-(benzyloxy)-3-methoxybenzoate (78 g) was mixed with dichloromethane (580 ml), water (72 ml) and glacial acetic acid (288 ml). The mixture was cooled to 10° C. Concentrated sulfuric acid (108 ml) was added in a controlled manner maintaining the temperature of the reaction mixture below 25° C. Concentrated nitric acid (17.5 ml) was then added keeping the temperature of the reaction mixture below 20° C. The reaction mixture was then stirred at 20° C. for 23 hours. The lower aqueous layer was removed and the organic layer was washed with water (290 ml). The organic layer was separated and distilled to 270 ml at atmospheric pressure. Isopropanol (750 ml) was added to the reaction mixture at 45° C. The reaction mixture was then heated to 40° C. and stirred at this temperature for 15 minutes. The resulting suspension was then cooled to 20° C., then to 5° C. and held at this temperature for one hour. The product (benzyl 4-(benzyloxy)-5-methoxy-2-nitrobenzoate) was isolated by filtration, washed with isopropanol (200 ml) and dried at less than 25° C. Yield: 78.4 g, 89.6%; NMR Spectrum (CDCl$_3$) 3.9 (s, 3H), 5.2 (s, 2H), 5.3 (s, 2H), 7.1 (s, 1H), 7.3-7.4 (m, 10H), 7.5 (s, 1H); Mass Spectrum (M+H)$^+$=394.1.

Benzyl 4-(benzyloxy)-5-methoxy-2-nitrobenzoate (77 g) was dissolved in acetonitrile (882 ml). Sodium dithionite (160.5 g) was added to the solution and the temperature adjusted to 25° C. Water (588 ml) was then added, maintaining the temperature at 25° C. The pH was maintained at 6 using 8.8 M sodium hydroxide during the reduction. The slurry was then heated to 65° C. and the lower aqueous phase was removed. Concentrated hydrochloric acid (35% w/w, 7.25 ml) was then added. The slurry was allowed to cool to 40° C. and then to 20° C. Sodium hydroxide solution (47% w/w, 12.4 ml) was added and the slurry cooled to 0° C. The product (benzyl 2-amino-4-(benzyloxy)-5-methoxybenzoate) was isolated by filtration, washed with water (2×196 ml) and then dried at 40° C. under vacuum. Yield: 66.2 g, 92.4%; NMR Spectrum (CDCl$_3$) 3.8 (s, 3H), 5.1 (s, 2H), 5.3 (s, 2H), 6.2 (s, 1H), 7.3-7.4 (m, 10H); Mass Spectrum (M+H)$^+$=364.1.

Benzyl 2-amino-4-(benzyloxy)-5-methoxybenzoate (5.55 kg), formamidine acetate (2.2 kg) and isobutanol (33.3 L) were mixed. The reaction mixture was then heated to 97° C. and stirred at this temperature for 6 hours. The reaction mixture was then cooled to 25° C. over a period of at least an hour and then stirred at this temperature for 30 minutes. The product (7-benzyloxy-6-methoxy-3,4-dihydroquinazolin-4-one) was isolated by filtration, washed with isobutanol (6.1 L) and dried in the vacuum oven at a temperature of from 40 to 45° C. Yield: 4.25 kg, 98%; NMR Spectrum (DMSOd$_6$) 3.9 (s, 3H), 5.3 (s, 2H), 7.3 (s, 1H), 7.3-7.5 (m, 6H), 8.0 (s, 1H); Mass Spectrum (M+H)$^+$=283.1.

The 7-benzyloxy-6-methoxy-3,4-dihydroquinazolin-4-one starting material was additionally prepared as follows:

A mixture of vanillic acid (20 g), acetonitrile (60 ml) and N-ethyldiisopropylamine (58 ml) was heated to reflux. Benzyl bromide (34.7 ml) was then added within 15 minutes. The reaction mixture was held at reflux for about 10 hours. Triethylamine (5 ml) was added and the reaction mixture held at reflux for a further 30 minutes. Acetonitrile (40 ml) and water (30 ml) were added and the reaction mixture cooled to 45° C. The reaction mixture was held at 45° C. until crystallisation occurred. The reaction mixture was then allowed to cool to 24° C. and then further cooled to 8° C. and the product (benzyl 4-(benzyloxy)-3-methoxybenzoate) isolated by filtration. The solid was washed with water (3×50 ml) and then dried under vacuum at 45° C. Yield: 38.7 g, 93%; NMR Spectrum (CDCl$_3$) 3.9 (s, 3H), 5.2 (s, 2H), 5.3 (s, 2H), 6.9 (d, 1H), 7.2-7.4 (m, 10H), 7.6-7.7 (m, 2H); Mass Spectrum (M+H)$^+$=349.2.

Benzyl 4-(benzyloxy)-3-methoxybenzoate (135 g) was dissolved in dichloromethane (339 ml). Glacial acetic acid (175.5 g) was added and the mixture cooled to 10° C. Concentrated sulfuric acid (151.6 g) was added in a controlled manner maintaining the temperature of the reaction mixture below 25° C. Concentrated nitric acid (61.6 g) was then added in 15 minutes keeping the temperature of the reaction mixture below 25° C. The reaction mixture was then heated to 40° C. and stirred for 3 hours. The lower aqueous layer was removed and the organic layer was washed twice with water (2×168 ml). The organic layer was distilled to at atmospheric pressure to remove dichloromethane (186 ml). Isopropanol (339 ml) was added to the reaction mixture at 40° C. The reaction mixture was held at 40° C. for 15 minutes. The resulting suspension was then cooled to 20° C. within 30 minutes, then to 5° C. and held at this temperature for one hour. The product (benzyl 4-(benzyloxy)-5-methoxy-2-nitrobenzoate) was isolated by filtration, washed with isopropanol (336 ml) and dried at less than 25° C. Yield: 135.7 g, 89.6%; NMR Spectrum (CDCl$_3$) 3.9 (s, 3H), 5.2 (s, 2H), 5.3 (s, 2H), 7.1 (s, 1H), 7.3-7.4 (m, 10H), 7.5 (s, 1H); Mass Spectrum (M+H)$^+$=394.1.

Benzyl 4-(benzyloxy)-5-methoxy-2-nitrobenzoate (90 g) was charged to acetonitrile (660 g). 85% Sodium dithionite (75 g) was added to the solution and the temperature adjusted to 20° C. Water (516 g) was then added, maintaining the temperature at 20° C. The slurry was then heated to 65° C. and stirred for 30 minutes. Sodium dithionite (75 g) was added and the mixture stirred for another 30 minutes. The lower aqueous phase was removed. Concentrated hydrochloric acid (33% w/w, 12.48 g) was then added to adjust to a pH of <1. The suspension is held for 1 hour. The slurry was cooled to 20° C. over 30 minutes. Sodium hydroxide solution (20% w/w, 59.29 g) was added to give a pH of 10. The slurry was cooled to 0° C. and stirred for one hour. The product (benzyl 2-amino-4-(benzyloxy)-5-methoxybenzoate) was isolated by filtration, washed twice with water (2×222 ml) and then dried at 60° C. under vacuum. Yield: 78.81 g, 95%; NMR Spectrum (CDCl$_3$) 3.8 (s, 3H), 5.1 (s, 2H), 5.3 (s, 2H), 6.2 (s, 1H), 7.3-7.4 (m, 10H); Mass Spectrum (M+H)$^+$=364.1.

Benzyl 2-amino-4-(benzyloxy)-5-methoxybenzoate (80.0 g), formamidine acetate (32.0 g) and isobutanol (480 ml) were mixed. The reaction mixture was then heated to 97° C. and stirred at this temperature for 6 hours. The reaction mixture was then cooled to 25° C. over a period of at least an hour and then stirred at this temperature for 30 minutes. The product (7-benzyloxy-6-methoxy-3,4-dihydroquinazolin-4-one) was isolated by filtration, washed with isobutanol (64.2 g) and dried in the vacuum oven at a temperature of from 40 to 45° C. Yield: 60.8 g, 98%; NMR Spectrum (DMSOd$_6$) 3.9 (s, 3H), 5.3 (s, 2H), 7.3 (s, 1H), 7.3-7.5 (m, 6H), 8.0 (s, 1H); Mass Spectrum (M+H)$^+$=283.1.

EXAMPLE 3

Preparation of the hydrochloride salt of 7-benzyloxy-4-(4-bromo-2-fluoroanilino)-6-methoxyquinazoline (the Hydrochloride Salt of the Compound of the Formula VI)

7-Benzyloxy-6-methoxy-3,4-dihydroquinazolin-4-one (20.00 g) was mixed with toluene (190 ml) and N,N-diisopropylethylamine (13.74 g). The reaction mixture was inserted with nitrogen and cooled to 15° C. Phosphorus oxychloride (19.8 g) was charged to the reaction mixture over a period of 15 minutes, followed by toluene (10 ml) as a wash. The reaction mixture was stirred for 15 minutes at 15° C. and then heated to 80° C. over a period of 90 minutes. The reaction mixture was then stirred at 80° C. for two hours. A solution of 4-bromo-2-fluoroaniline (16.8 g) in toluene (40 ml) was added to the reaction mixture over a period of 40 minutes, followed by toluene (10 ml) as a wash. The reaction mixture was then stirred at 80° C. for 4 hours.

The reaction mixture was then cooled to 25° C. and the product isolated by filtration. The filter cake was washed twice with water (2×40 ml). Yield: 34.37 g, 87%; NMR Spectrum (DMSOd$_6$, CD$_3$COOD) 4.0 (s, 3H), 5.37 (s, 2H), 7.35-7.5 (m, 4H), 7.52-7.62 (m, 4H), 7.8 (d, 1H), 8.14 (s, 1H), 8.79 (s, 1H); Mass Spectrum [ESI] (M+H)$^+$=454.0591.

EXAMPLE 4

Preparation of trifluoroacetic acid salt of 7-hydroxy-4-(4-bromo-2-fluoroanilino)-6-methoxyquinazoline (the Trifluoroacetic Acid Salt of the Compound of the Formula IX)

7-benzyloxy-6-methoxy-3,4-dihydroquinazolin-4-one (100 g), triethylamine (59.3 ml) and toluene (650 ml) were charged to a vessel and inserted with nitrogen. The contents were heated to 40° C. and charged over a period of about 40 minutes to a solution of phosphorus oxychloride (97.7 g) in toluene (400 ml) held at 73° C. in a vessel inserted with nitrogen. The reaction mixture was then held at a temperature of about 73° C. for a period of about 90 minutes. 4-Bromo-2-fluoroaniline (84.1 g) was dissolved in toluene (250 ml) and charged to the reaction mixture at 73° C. and held stirring at this temperature for about 4 hours. Trifluoroacetic acid (350 ml) was then added to the reaction mixture at 73° C. and the reaction mixture stirred at 73° C. for 6 hours and then cooled to 60° C. Water (1750 ml) was added to the reaction mixture and the temperature held at 60° C. for about 30 minutes and then warmed to 70° C. and stirred at 70° C. for about 22 hours. The reaction mixture was then cooled to 20° C. and the product isolated by filtration, washed with water (200 ml) and dried at 50° C. Yield: 120 g, 93%; NMR Spectrum (DMSOd$_6$) 4.0 (s, 3H), 7.24 (s, 1H), 7.56 (m, 2H), 7.78 (d, 1H), 8.02 (s, 1H), 8.73 (s, 1H); Mass Spectrum (M+H)$^+$=454.0591.

EXAMPLE 5

Preparation of trifluoroacetic acid salt of 7-hydroxy-4-(4-bromo-2-fluoroanilino)-6-methoxyquinazoline (the Trifluoroacetic Acid Salt of the Compound of the Formula IX)

7-benzyloxy-6-methoxy-3,4-dihydroquinazolin-4-one (15 g), triethylamine (9.0 ml) and toluene (90 ml) were charged to a vessel and inserted with nitrogen. The contents were held at ambient and charged over a period of about 40 minutes to a solution of phosphorus oxychloride (14.7 g) in toluene (60 ml) held at 73° C. in a vessel inserted with nitrogen. This was followed by a toluene (7.5 ml) line wash. The reaction mixture was then held at a temperature of about 73° C. for a period of about 90 minutes. 4-Bromo-2-fluoroaniline (12.6 g) was dissolved in toluene (30 ml) and charged to the reaction mixture at 73° C. and held stirring at this temperature for about 4 hours. Trifluoroacetic acid (60 ml) was then added to the reaction mixture at 73° C. and the reaction mixture stirred at 73° C. for 6 hours and then cooled to 60° C. Potassium hydroxide (48-50% w/w, 16.1 ml) in water (10.5 ml) was charge over approximately 30 minutes followed by a hour hold at 60° C. Water (180 ml) was added to the reaction mixture over approximately 70 minutes followed by 7-hydroxy-4-(4-bromo-2-fluoroanilino)-6-methoxyquinazoline trifluoroacetic acid salt seed (0.13 g). The batch was held at 60° C. for about 60 minutes and then water (60 ml) was added over approximately 20 minutes. The reaction mixture was held for approximately two hours

EXAMPLE 6

Preparation of a hydrogen chloride salt of 7-hydroxy-4-(4-bromo-2-fluoroanilino)-6-methoxyquinazoline (the Hydrogen Chloride Salt of the Compound of the Formula IX)

7-benzyloxy-6-methoxy-3,4-dihydroquinazolin-4-one (30.00 g) was mixed with triethylamine hydrochloride (2.99 g), anisole (285 ml) and N,N-diisopropylethylamine (20.71 g). The reaction mixture was inserted with nitrogen and cooled to 15° C. Phosphorus oxychloride (21.4 g) was added to the reaction mixture over a period of 15 minutes followed by an anisole (30 ml) wash. The reaction mixture was then stirred for 15 minutes at 15° C. and then heated to 80° C. over a period of 90 minutes. The reaction mixture was stirred at 80° C. for one hour. A solution of 4-bromo-2-fluoroaniline (25.2 g) in anisole (15 ml) was added to the reaction mixture over a period of 25 minutes. The reaction mixture was stirred for 4 hours at 80° C. Aqueous hydrogen chloride (35% w/w, 122 ml) and acetic acid (198 ml) were charged to the reaction mixture. The reaction mixture was stirred for 3 hours and then the anisole layer was removed. The reaction mixture was cooled to 25° C. and the solid isolated by filtration. Yield: 13.9 g, 54%; NMR Spectrum (DMSOd$_6$) 4.0 (s, 3H), 7.43 (s, 1H), 7.5 (m, 2H), 7.7 (d, 1H), 8.37 (s, 1H), 8.72 (s, 1H); Mass Spectrum (M+H)$^+$=454.0591.

EXAMPLE 7

Preparation of hydrogen chloride salt of 7-hydroxy-4-(4-bromo-2-fluoroanilino)-6-methoxyquinazoline (the Hydrogen Chloride Salt of the Compound of the Formula IX)

Phosphorus oxychloride (6.0 ml) was added over a period of 60 minutes to a stirred slurry of 7-benzyloxy-6-methoxy-3,4-dihydroquinazolin-4-one (10.0 g) and N,N-diisopropylethylamine (7.45 ml) in toluene (105 ml) at 20° C. After stirring the reaction mixture for 30 minutes at 20° C., the reaction mixture was heated over a period of 90 minutes to 73° C. and then stirred for a further 3 hours at that temperature. 4-bromo-2-fluoroaniline (8.4 g) in toluene (20 ml) was added to the reaction mixture at 73° C., followed by a toluene wash (5 ml). Trifluoroacetic acid (35 ml, 3.5 vol) was added over a period of 10 minutes to the reaction mixture at 73° C. and the reaction mixture was then stirred at that temperature for 5 hours. The reaction mixture was then cooled to 60° C. and water (175 ml) was added over a period of 15 minutes. The reaction mixture was then warmed to 68° C. and stirred at that temperature for 8 hours. The reaction mixture was then cooled to 20° C. over a period of 1 hour and the product was filtered off and washed with water (20 ml). Yield: 11.56 g, 90%; NMR Spectrum (DMSOd$_6$) 4.0 (s, 3H), 7.43 (s, 1H), 7.5 (m, 2H), 7.7 (d, 1H), 8.37 (s, 1H), 8.72 (s, 1H); Mass Spectrum (M+H)$^+$=454.0591.

EXAMPLE 8

Preparation of trifluoroacetic acid salt of 7-hydroxy-4-(4-bromo-2-fluoroanilino)-6-methoxyquinazoline (the Trifluoroacetic Acid Salt of the Compound of the Formula IX)

Phosphorus oxychloride (6.0 ml) was added over a period of 15 minutes to a stirred slurry of 7-benzyloxy-6-methoxy-3,4-dihydroquinazolin-4-one (10.0 g) and triethylamine (5.9 ml) in toluene (105 ml) at 73° C. and the reaction mixture stirred for a further 3 hours. 4-bromo-2-fluoroaniline (8.4 g) in toluene (20 ml) was added to the reaction mixture at 73° C., followed by a toluene wash (5 ml). Trifluoroacetic acid (35 ml, 3.5 vol) was then added over a period of 10 minutes to the reaction mixture at 73° C. and the reaction mixture was then stirred at that temperature for a further 5 hours. The reaction mixture was cooled to 60° C. and water (175 ml) was added over a period of 15 minutes. The reaction mixture was then warmed to 68° C. and stirred at that temperature for 8 hours. The slurry was cooled to 20° C. over 1 hour and the product was filtered off and washed with water (20 ml). Yield: 11.24 g, 87%; NMR Spectrum (DMSOd$_6$) 8.72 (1H, s), 8.02 (1H, s), 7.76-7.73 (1H, m), 7.56-7.50 (2H, m), 7.25 (1H, s), 3.97 (3H, s); Mass Spectrum (M+H)$^+$=454.0591.

EXAMPLE 9

Preparation of 7-(1-tert-butoxycarbonyl)piperidine-4-ylmethoxy)-4-(4-bromo-2-fluoroanilino)-6-methoxyquinazoline (the Compound of the Formula X)

7-hydroxy-4-(4-bromo-2-fluoroanilino)-6-methoxyquinazoline (100 g) and potassium carbonate (113.8 g) were suspended in N-methylpyrrolidinone (1070 ml) and stirred for 10 minutes prior to the addition of 1-(tert-butoxycarbonyl)-4-(4-methylphenylsulfonyloxymethyl)piperidine (152.2 g). The reaction mixture was then heated to 95° C. for 4 hours before being cooled back to 70° C. Water (1922 ml) was then added over a period of 15 minutes. The reaction mixture was held at 73° C. for 1 hour before being cooled to 40° C. and the product isolated by filtration. The product was washed with water (549 ml), slurry washed with ethyl acetate (549 ml) at 50° C. for 1 hour and then washed with ethyl acetate (275 ml) and dried at 50° C. Yield: 137 g, 86%; NMR Spectrum (DMSOd$_6$) 1.15-1.3 (m, 2H), 1.46 (s, 9H), 1.8 (d, 2H), 2.0-2.1 (m, 1H), 2.65-2.9 (m, 2H) 3.95 (s, 3H), 4.02 (br s, 2H), 4.05 (d, 2H), 7.2 (s, 1H), 7.48 (d, 1H), 7.55 (t, 1H), 7.65 (d, 1H), 7.8 (d, 1H), 8.35 (s, 1H), 9.55 (br s, 1H); Mass Spectrum [ESI] (M+H)$^+$=561-563.

EXAMPLE 10

Preparation of 7-(1-tert-butoxycarbonyl)piperidine-4-ylmethoxy)-4-(4-bromo-2-fluoroanilino)-6-methoxyquinazoline (the Compound of the Formula X)

7-hydroxy-4-(4-bromo-2-fluoroanilino)-6-methoxyquinazoline (5.0 g) and potassium carbonate (5.7 g) were suspended in N-methylpyrrolidinone (53.5 ml) and stirred for 10 minutes. 1-(tert-butoxycarbonyl)-4-(4-methylphenylsulfonyloxymethyl)piperidine (7.6 g) was then added. The reaction mixture was then heated to 95° C. and stirred at that temperature for 3.5 hours before being cooled back to 70° C. Isopropanol (25 ml) was added and then water (75 ml) was added over a period of 15 minutes. The reaction mixture was then stirred at 73° C. for 1 hour before cooling to 40° C. and isolation of the product by filtration. The product was washed with water (27.4 ml) and dried at 50° C. Yield: 6.72 g, 87.2%; NMR Spectrum (DMSOd$_6$) 1.15-1.3 (m, 2H), 1.46 (s, 9H), 1.8 (d, 2H), 2.0-2.1 (m, 1H), 2.65-2.9 (m, 2H) 3.95 (s, 3H), 4.02 (br s, 2H), 4.05 (d, 2H), 7.2 (s, 1H), 7.48 (d, 1H), 7.55 (t, 1H), 7.65 (d, 1H), 7.8 (d, 1H), 8.35 (s, 1H), 9.55 (br s, 1H); Mass Spectrum [ESI] (M+H)$^+$=561-563.

EXAMPLE 11

Preparation of 7-(1-tert-butoxycarbonyl)piperidine-4-ylmethoxy)-4-(4-bromo-2-fluoroanilino)-6-methoxyquinazoline (the Compound of the Formula X)

7-hydroxy-4-(4-bromo-2-fluoroanilino)-6-methoxyquinazoline (9.7 g), sodium hydroxide (47% w/w, 5.0 ml) and Adogen® 464 (1.5 g) were added to water (50 ml) with stirring. 1-(tert-butoxycarbonyl)-4-(4-methylphenylsulfonyloxymethyl)piperidine (10.0 g) as a solution in toluene (35 ml) was then added to the reaction mixture and heated to 70° C. for 18 hours. The reaction mixture was then cooled to 20° C. and the product was isolated by filtration. The product was then washed with toluene (20 ml) and dried at 50° C. Yield: 8.72 g, 77%; NMR Spectrum (DMSOd$_6$) 1.15-1.3 (m, 2H), 1.46 (s, 9H), 1.8 (d, 2H), 2.0-2.1 (m, 1H), 2.65-2.9 (m, 2H) 3.95 (s, 3H), 4.02 (br s, 2H), 4.05 (d, 2H), 7.2 (s, 1H), 7.48 (d, 1H), 7.55 (t, 1H), 7.65 (d, 1H), 7.8 (d, 1H), 8.35 (s, 1H), 9.55 (br s, 1H); Mass Spectrum [ESI] (M+H)$^+$=561-563.

EXAMPLE 12

Preparation of 4-(4-bromo-2-fluoroanilino)-6-methoxy-7-(1-methylpiperidin-4-ylmethoxy)quinazoline (ZD6474)

7-(1-tert-butoxycarbonyl)piperidine-4-ylmethoxy)-4-(4-bromo-2-fluoroanilino)-6-methoxyquinazoline (100 g), water (80 ml), formic acid (120 ml) and aqueous formaldehyde (38% w/w, 28.2 g) were added to a vessel equipped with overhead stirrer, reflux condenser and purged with nitrogen. The reaction mixture was heated to 80° C. over a period of 90 minutes and stirred at this temperature for 5 hours. The reaction mixture was then cooled to 20° C. and tetrahydrofuran (500 ml) was added. The reaction mixture was warmed to 40° C. and sodium hydroxide (47% w/w, 265 ml) was added, followed by water (60 ml). The aqueous phase was separated and discarded. The organic phase was adjusted to 60° C. and water (300 ml) and butyl acetate (300 ml) were added. The resulting mixture was stirred at 60° C. for 15 minutes and then the aqueous phase separated and discarded. Water (400 ml) was then added to the organic phase, which was stirred at 60° C. for 15 minutes and then the aqueous phase separated and discarded. Butyl acetate (300 ml) and tetrahydrofuran (50 ml) were added to the organic phase and set for distillation at ambient pressure. The distillation was stopped when the contents temperature reached 104° C. The slurry was then cooled to 20° C. and held for 2 hours before isolating the product by filtration. The product was washed with butyl acetate (300 ml) and dried at 50° C. Yield: 76.7 g, 90.6%; NMR Spectrum (pyridine-d5) 1.49 (2H, m), 1.75-1.90 (5H, m), 2.15 (3H, s), 2.76 (2H, m), 3.63 (3H, s), 3.97 (2H, d), 7.38 (1H, ddd), 7.49 (1H, dd), 7.64 (1H, s), 7.88 (1H, t), 7.89 (1H, s), 9.01 (1H, s), 10.37 (1H, s); Mass Spectrum (M+H)$^+$=475.

EXAMPLE 13

Preparation of 4-(4-bromo-2-fluoroanilino)-6-methoxy-7-(1-methylpiperidin-4-ylmethoxy)quinazoline (ZD6474)

7-(1-tert-butoxycarbonyl)piperidine-4-ylmethoxy)-4-(4-bromo-2-fluoroanilino)-6-methoxyquinazoline (35.0 g), water (28 ml), formic acid (42 ml) and aqueous formaldehyde (37% w/w, 8.2 g) were added to a vessel equipped with overhead stirrer, reflux condenser and purged with nitrogen. The reaction mixture was heated to 80° C. and stirred at this temperature for 5 hours. The reaction mixture was then cooled to 40° C. and tetrahydrofuran (175 ml) was added. Sodium hydroxide (47% w/w, 61.9 ml) was added at 40° C. followed by water (21 ml). The aqueous phase was then separated and discarded. Water (420 ml) was added to the organic phase at 40° C. over a period of 30 minutes. The slurry was then cooled to 20° C. before isolating the product by filtration. The product was washed with water (175 ml) and dried at 50° C. Yield: 27.1 g, 91.4%; NMR Spectrum (pyridine-d5) 1.49 (2H, m), 1.75-1.90 (5H, m), 2.15 (3H, s), 2.76 (2H, m), 3.63 (3H, s), 3.97 (2H, d), 7.38 (1H, ddd), 7.49 (1H, dd), 7.64 (1H, s), 7.88 (1H, t), 7.89 (1H, s), 9.01 (1H, s), 10.37 (1H, s); Mass Spectrum (M+H)$^+$=475.

EXAMPLE 14

Preparation of 4-(4-bromo-2-fluoroanilino)-6-methoxy-7-(1-methylpiperidin-4-ylmethoxy)quinazoline (ZD6474)

7-(1-tert-butoxycarbonyl)piperidine-4-ylmethoxy)-4-(4-bromo-2-fluoroanilino)-6-methoxyquinazoline (100 g), water (80 ml), formic acid (120 ml) and aqueous formaldehyde (37% w/w, 26.7 g) were added to a vessel equipped with overhead stirrer, reflux condenser and purged with nitrogen. The reaction mixture was heated to 80° C. over a period of 90 minutes and stirred at this temperature for 5 hours. The reaction mixture was then cooled to 60° C. and methanol (800 ml) was added, followed by potassium hydroxide (49% w/w, 228 ml) over 2 hours. The slurry was cooled to 20° C. over 2 hours before isolating the product by filtration. The product was washed twice with aqueous methanol (2:1 methanol:water, 300 ml) and dried at 50° C. Yield: 79.6 g, 94%; NMR Spectrum (pyridine-d5) 1.49 (2H, m), 1.75-1.90 (5H, m), 2.15 (3H, s), 2.76 (2H, m), 3.63 (3H, s), 3.97 (2H, d), 7.38 (1H, ddd), 7.49 (1H, dd), 7.64 (1H, s), 7.88 (1H, t), 7.89 (1H, s), 9.01 (1H, s), 10.37 (1H, s); Mass Spectrum (M+H)$^+$=475.

EXAMPLE 15

Preparation of 4-(4-bromo-2-fluoroanilino)-6-methoxy-7-(1-methylpiperidin-4-ylmethoxy)quinazoline (ZD6474)

7-(1-tert-butoxycarbonyl)piperidine-4-ylmethoxy)-4-(4-bromo-2-fluoroanilino)-6-methoxyquinazoline (100 g), water (45 ml), formic acid (120 ml) and aqueous formaldehyde (37% w/w, 101.8 g) were added to a vessel equipped with an overhead stirrer and a reflux condenser and purged with nitrogen. The reaction mixture was heated to 80° C. over a period of 90 minutes and stirred at this temperature for 5 hours. The reaction mixture was then cooled to 60° C. and methanol (800 ml) was added, followed by potassium hydroxide (49% w/w, 228 ml) over 2 hours. The slurry was cooled to 20° C. over 2 hours before isolating the product by filtration. The product was washed twice with aqueous methanol (2:1 methanol:water, 300 ml) and dried at 50° C. Yield: 79.6 g, 94%; NMR Spectrum (pyridine-d5) 1.49 (2H, m), 1.75-1.90 (5H, m), 2.15 (3H, s), 2.76 (2H, m), 3.63 (3H, s), 3.97 (2H, d), 7.38 (1H, ddd), 7.49 (1H, dd), 7.64 (1H, s), 7.88 (1H, t), 7.89 (1H, s), 9.01 (1H, s), 10.37 (1H, s); Mass Spectrum (M+H)$^+$=475.

EXAMPLE 16

Preparation of 4-(4-bromo-2-fluoroanilino)-6-methoxy-7-(1-methylpiperidin-4-ylmethoxy)quinazoline (ZD6474)

7-(1-tert-butoxycarbonyl)piperidine-4-ylmethoxy)-4-(4-bromo-2-fluoroanilino)-6-methoxyquinazoline (36 g @ 100% w/w), water (16 ml), formic acid (44 ml) and aqueous formaldehyde (37% w/w, 36.4 g) were added to a vessel equipped with an overhead stirrer and a reflux condenser and purged with nitrogen. The reaction mixture was heated to 80° C. over a period of 90 minutes and stirred at this temperature for 7 hours. The reaction mixture was then cooled to 60° C. and methanol (376 ml) was added, followed by potassium hydroxide (49% w/w, 86 ml) over 2 hours. The slurry was seeded with ZD6474 (methanolate form, 300 mg) and cooled to 20° C. over 2 hours before isolating the product by filtration. The product was washed twice with aqueous methanol (80:20 methanol:water, 67 ml) and dried at ambient temperature. Yield: 32.4 g, 95%; NMR Spectrum (pyridine-d5) 1.49 (2H, m), 1.75-1.90 (5H, m), 2.15 (3H, s), 2.76 (2H, m), 3.63 (3H, s), 3.97 (2H, d), 7.38 (1H, ddd), 7.49 (1H, dd), 7.64 (1H, s), 7.88 (1H, t), 7.89 (1H, s), 9.01 (1H, s), 10.37 (1H, s); Mass Spectrum (M+H)$^+$=475.

EXAMPLE 17

Purification of 4-(4-bromo-2-fluoroanilino)-6-methoxy-7-(1-methylpiperidin-4-ylmethoxy)quinazoline (ZD6474)

4-(4-bromo-2-fluoroanilino)-6-methoxy-7-(1-methylpiperidin-4-ylmethoxy)quinazoline prepared as described in Example 9 (100 g) was suspended in tetrahydrofuran (500 ml), water (250 ml) and butyl acetate (400 ml) and heated to reflux to allow dissolution. The mixture was then cooled to 60° C. and the aqueous phase separated and discarded. The organic phase was filtered. Tetrahydrofuran (50 ml) and butyl acetate (600 ml) were added to the organic filtrates and then heated to distil at ambient pressure until an internal temperature of 106° C. was reached. The slurry was then cooled to 5° C., filtered and washed with ethyl acetate (200 ml). The product was dried at 50° C. Yield: 91.8 g, 91.8%; NMR Spectrum (pyridine-d5) 1.49 (2H, m), 1.75-1.90 (5H, in), 2.15 (3H, s), 2.76 (2H, m), 3.63 (3H, s), 3.97 (2H, d), 7.38 (1H, ddd), 7.49 (1H, dd), 7.64 (1H, s), 7.88 (1H, t), 7.89 (1H, s), 9.01 (1H, s), 10.37 (1H, s); Mass Spectrum (M+H)$^+$=475.

EXAMPLE 18

Preparation of 4-(4-bromo-2-fluoroanilino)-6-methoxy-7-(1-methylpiperidin-4-ylmethoxy)quinazoline (ZD6474)

7-(1-tert-butoxycarbonyl)piperidine-4-ylmethoxy)-4-(4-bromo-2-fluoroanilino)-6-methoxyquinazoline (40 g), water (16 ml), formic acid (43 ml) and aqueous formaldehyde (37% w/w, 33 ml) were added to a vessel equipped with overhead stirrer, reflux condenser and thermometer. The reaction mixture was heated to 81° C. and stirred at this temperature for 5 hours. The reaction mixture was cooled to 60° C. and tetrahydrofuran (178 ml) was added. The temperature of the reaction mixture was adjusted to 40° C. and potassium hydroxide (49% w/w, 84 ml) was added, followed by water (22 ml). The aqueous phase was separated and discarded. The organic phase was adjusted to 60° C. and water (107 ml) and butyl acetate (107 ml) were added. The aqueous phase was separated and discarded. The organic phase was filtered, following through with tetrahydrofuran (18 ml) wash. The temperature of the filtrates was adjusted to 60° C. and butyl acetate (107 ml) was added. The reaction mixture was set for distillation at ambient pressure. The distillation was stopped when the contents temperature reached 106° C. The slurry was cooled to 65° C. and tetrahydrofuran (107 ml) was added. The slurry was cooled to 0-5° C. and held for 1 hour before isolating the product by filtration. The product was washed with ethyl acetate (72 ml) and dried at 50° C. Yield: 24.82 g, 80.3%.

EXAMPLE 19

X-Ray Powder Diffraction of Anhydrous ZD6474

The processes of the present invention synthesize the anhydrous from of ZD6474. The anhydrous form of ZD6474 is characterised by X-Ray powder diffraction and is characterised in providing at least one of the following 2 theta values measured using CuKα, radiation: 15.0° and 21.4°. The anhydrous form of ZD6474 is characterised in providing a CuKα X-ray powder diffraction pattern as shown in FIG. 1. The ten most prominent peaks are shown in Table 1.

TABLE 1

Ten most prominent X-Ray Powder Diffraction peaks for the anhydrous form of ZD6474

| Angle 2-Theta (° 2θ) | Intensity Count | Relative Intensity |
|---|---|---|
| 15.0 | 100 | vs |
| 21.4 | 92.8 | vs |
| 23.3 | 63.7 | vs |
| 20.7 | 48.3 | vs |
| 18.9 | 40.4 | vs |
| 18.1 | 40.1 | vs |
| 23.7 | 39.2 | vs |
| 8.3 | 28.9 | vs |
| 22.1 | 25.9 | vs |
| 29.5 | 23.2 | s | vs = very strong;
s = strong

TABLE 2

| % Relative Intensity* | Definition |
|---|---|
| 25-100 | vs (very strong) |
| 10-25 | s (strong) |
| 3-10 | m (medium) |
| 1-3 | w (weak) |

*The relative intensities are derived from diffractograms measured with fixed slits.

Analytical Instrument: Siemens D5000, calibrated using quartz.

The X-ray powder diffraction spectra is determined by mounting a sample of the crystalline ZD6474 material on Siemens single silicon crystal (SSC) wafer mounts and spreading out the sample into a thin layer with the aid of a microscope slide. The sample is spun at 30 revolutions per minute (to improve counting statistics) and is irradiated with X-rays generated by a copper long-fine focus tube operated at 40 kV and 40 mA using CuKα radiation with a wavelength of 1.5406 angstroms. The collimated X-ray source is passed through an automatic variable divergence slit set at V20 and the reflected radiation is directed through a 2 mm antiscatter slit and a 0.2 mm detector slit. The sample is exposed for 1 second per 0.02 degree 2-theta increment (continuous scan mode) over the range 2 degrees to 40 degrees 2-theta in theta-theta mode. The running time is 31 minutes and 41 seconds. The instrument is equipped with a scintillation counter as detector. Control and data capture is by means of a Dell Optiplex 686 NT 4.0 Workstation operating with Diffract+software. Persons skilled in the art of X-ray powder diffraction will realise that the relative intensity of peaks can be affected by, for example, grains above 30 microns in size and non-unitary aspect ratios which may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values.

For more information on X-ray powder diffraction the reader is referred to Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures.

BRIEF DESCRIPTION OF THE DRAWINGS

FIG. 1: X-Ray Powder Diffraction Pattern for ZD6474 anhydrous—with the 2 theta values plotted on the horizontal axis and the relative line intensity (counts) plotted on the vertical axis.

The invention claimed is:

1. A process for the manufacture of a compound of the Formula VI:

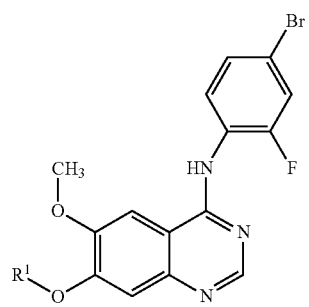

wherein $R^1$ is an acid labile protecting group from a compound of the Formula VII:

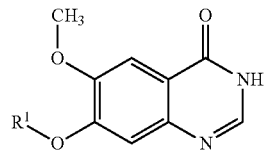

which process comprises the steps of:
(g) reacting the compound of the Formula VII with a suitable chlorinating agent in the presence of a suitable base and a suitable solvent, wherein the reaction is carried out by:
  (g-1) adding a mixture of the compound of the Formula VII and the base in the solvent to a mixture of the chlorinating agent in the solvent at a temperature in the range of from 60 to 90° C. over a period of about 60 minutes; or
  (g-2) adding the chlorinating agent to a mixture of the compound of the Formula VII and the base in the solvent at ambient temperature over a period of about 15 minutes and then heating the reaction mixture over a period of about 90 minutes to a temperature in the range of from 70 to 90° C. and stirring the reaction mixture at that temperature for about 1 hour; or
  (g-3) adding the chlorinating agent to a mixture of the compound of the Formula VII and the base in the solvent at a temperature in the range of from 60 to 110° C. over a period of about 15 minutes,
to form a compound of the Formula VIII:

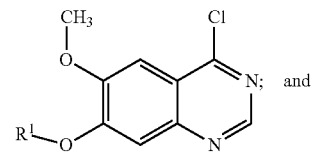

(h) reacting the compound of the Formula VIII with 4-bromo-2-fluoroaniline in situ in the presence of the solvent used in step (g) to form the compound of the Formula VI as a hydrochloride salt;
and whereafter the compound of the Formula VI obtained in the form of the hydrochloride salt optionally may be converted into the free base or into the form of an alternative salt.

2. The process according to claim 1, wherein steps (g) and (h) are both conducted in toluene.

3. The process according to claim 1, wherein the chlorinating agent used in step (g) is phosphorus oxychloride.

4. The process according to claim 1, wherein the base used in step (g) is selected from the group consisting of triethylamine and N,N-diisopropylethylamine.

5. The process according to claim 1, further comprising the step (i) of isolating the compound of the Formula VI.

* * * * *